(12) United States Patent
Chetham

(10) Patent No.: US 8,781,551 B2
(45) Date of Patent: Jul. 15, 2014

(54) APPARATUS FOR CONNECTING IMPEDANCE MEASUREMENT APPARATUS TO AN ELECTRODE

(75) Inventor: Scott Matthew Chetham, Del Mar, CA (US)

(73) Assignee: Impedimed Limited, Pinkenba, Queensland (AU)

( * ) Notice: Subject to any disclaimer, the term of this patent is extended or adjusted under 35 U.S.C. 154(b) by 1482 days.

(21) Appl. No.: 11/993,842

(22) PCT Filed: Jun. 30, 2006

(86) PCT No.: PCT/AU2006/000923
§ 371 (c)(1),
(2), (4) Date: Nov. 6, 2008

(87) PCT Pub. No.: WO2007/002992
PCT Pub. Date: Jan. 11, 2007

(65) Prior Publication Data
US 2009/0143663 A1 Jun. 4, 2009

Related U.S. Application Data

(60) Provisional application No. 60/697,100, filed on Jul. 7, 2005, provisional application No. 60/703,270, filed on Jul. 28, 2005.

(30) Foreign Application Priority Data

Jul. 1, 2005 (AU) .................. 2005903510
Jul. 20, 2005 (AU) .................. 2005903887

(51) Int. Cl.
*A61B 5/053* (2006.01)
*H01R 13/66* (2006.01)
*H01R 4/48* (2006.01)

(52) U.S. Cl.
USPC ........... 600/372; 600/382; 600/547; 600/394; 439/620.22; 439/822; 439/909

(58) Field of Classification Search
USPC .......... 600/372, 382, 394, 506, 547; 607/115, 607/148; 439/278, 786, 822, 909, 620.22
See application file for complete search history.

(56) References Cited

U.S. PATENT DOCUMENTS 3,316,896 A   5/1967   Thomasset
3,851,641 A   12/1974  Toole et al.

(Continued)

FOREIGN PATENT DOCUMENTS

CA   2638958 A1   6/2000
CN   1180513 A    5/1998

(Continued)

OTHER PUBLICATIONS

Chetham, Matthew; U.S. Appl. No. 11/629,804 entitled "Cardiac monitoring system," filed Dec. 15, 2006.

(Continued)

*Primary Examiner* — Lee S Cohen
*Assistant Examiner* — Erin M Cardinal
(74) *Attorney, Agent, or Firm* — Knobbe Martens Olson & Bear LLP

(57) ABSTRACT

A method of monitoring pulmonary oedema in a subject using a processing system. The method includes, determining a measured impedance value for at least two body segments, at least one of the body segments being a thoracic cavity segment. For each body segment, the measured impedance values are used to determine an index, which is in turn used to determine the presence, absence or degree of pulmonary oedema using the determined indices.

10 Claims, 28 Drawing Sheets

(56) References Cited

U.S. PATENT DOCUMENTS

| | | | |
|---|---|---|---|
| RE30,101 E | 9/1979 | Kubicek et al. | |
| 4,353,372 A * | 10/1982 | Ayer | 600/393 |
| 4,450,527 A | 5/1984 | Sramek | |
| 4,486,835 A | 12/1984 | Bai et al. | |
| 4,695,955 A | 9/1987 | Faisandier | |
| 4,832,608 A * | 5/1989 | Kroll | 439/67 |
| 4,890,630 A | 1/1990 | Kroll et al. | |
| 4,905,705 A | 3/1990 | Kizakevich et al. | |
| 4,924,875 A | 5/1990 | Chamoun | |
| 5,063,937 A | 11/1991 | Ezenwa et al. | |
| 5,078,134 A * | 1/1992 | Heilman et al. | 607/4 |
| 5,086,781 A | 2/1992 | Bookspan | |
| 5,101,828 A | 4/1992 | Welkowitz et al. | |
| 5,199,432 A * | 4/1993 | Quedens et al. | 600/376 |
| 5,280,429 A | 1/1994 | Withers | |
| 5,309,917 A | 5/1994 | Wang et al. | |
| 5,423,326 A | 6/1995 | Wang et al. | |
| 5,449,000 A | 9/1995 | Libke et al. | |
| 5,454,377 A | 10/1995 | Dzwonczyk et al. | |
| 5,469,859 A | 11/1995 | Tsoglin et al. | |
| 5,503,157 A | 4/1996 | Sramek et al. | |
| 5,511,553 A * | 4/1996 | Segalowitz | 600/508 |
| 5,526,808 A | 6/1996 | Kaminsky | |
| 5,529,072 A | 6/1996 | Sramek | |
| 5,562,607 A * | 10/1996 | Gyory | 604/20 |
| 5,626,146 A | 5/1997 | Barber et al. | |
| 5,732,710 A | 3/1998 | Rabinovich et al. | |
| 5,735,284 A | 4/1998 | Tsoglin et al. | |
| 5,746,214 A | 5/1998 | Brown et al. | |
| 5,759,159 A | 6/1998 | Masreliez | |
| 5,788,643 A | 8/1998 | Feldman | |
| 5,807,272 A | 9/1998 | Kun et al. | |
| 5,876,353 A | 3/1999 | Riff | |
| 5,906,614 A | 5/1999 | Stern et al. | |
| 5,957,861 A | 9/1999 | Combs et al. | |
| 6,006,125 A * | 12/1999 | Kelly et al. | 600/382 |
| 6,018,677 A | 1/2000 | Vidrine et al. | |
| 6,125,297 A | 9/2000 | Siconolfi | |
| 6,142,949 A | 11/2000 | Ubby | |
| 6,151,523 A | 11/2000 | Rosell Ferrer et al. | |
| 6,208,890 B1 | 3/2001 | Sarrazin et al. | |
| 6,339,722 B1 | 1/2002 | Heethaar et al. | |
| 6,469,732 B1 | 10/2002 | Chang et al. | |
| 6,472,888 B2 | 10/2002 | Oguma et al. | |
| 6,496,725 B2 | 12/2002 | Kamada et al. | |
| 6,511,438 B2 | 1/2003 | Bernstein et al. | |
| 6,512,949 B1 | 1/2003 | Combs et al. | |
| 6,532,384 B1 | 3/2003 | Fukuda et al. | |
| 6,551,252 B2 | 4/2003 | Sackner et al. | |
| 6,556,001 B1 | 4/2003 | Wiegand et al. | |
| 6,560,480 B1 | 5/2003 | Nachaliel et al. | |
| 6,561,986 B2 | 5/2003 | Baura et al. | |
| 6,602,201 B1 | 8/2003 | Happ et al. | |
| 6,615,077 B1 | 9/2003 | Zhu et al. | |
| 6,623,312 B2 * | 9/2003 | Merry et al. | 439/729 |
| 6,631,292 B1 | 10/2003 | Liedtke | |
| 6,636,754 B1 | 10/2003 | Baura et al. | |
| 6,643,543 B2 | 11/2003 | Takehara et al. | |
| 6,714,813 B2 | 3/2004 | Ishigooka et al. | |
| 6,724,200 B2 | 4/2004 | Fukuda | |
| 6,725,089 B2 | 4/2004 | Komatsu et al. | |
| 6,760,617 B2 | 7/2004 | Ward et al. | |
| 6,790,178 B1 | 9/2004 | Mault et al. | |
| 6,807,443 B2 | 10/2004 | Keren | |
| 6,823,209 B2 * | 11/2004 | Olson et al. | 600/510 |
| 6,829,501 B2 | 12/2004 | Nielsen et al. | |
| 6,829,503 B2 | 12/2004 | Alt | |
| 6,980,852 B2 | 12/2005 | Jersey-Willuhn et al. | |
| 7,096,061 B2 | 8/2006 | Arad | |
| 7,122,012 B2 | 10/2006 | Bouton et al. | |
| 7,149,573 B2 | 12/2006 | Wang | |
| 7,169,107 B2 | 1/2007 | Jersey-Willuhn et al. | |
| 7,184,820 B2 | 2/2007 | Jersey-Willuhn et al. | |
| 7,184,821 B2 | 2/2007 | Belalcazar et al. | |
| 7,186,220 B2 | 3/2007 | Stahmann et al. | |
| 7,233,823 B2 | 6/2007 | Simond et al. | |
| 7,251,524 B1 | 7/2007 | Hepp et al. | |
| 7,749,013 B2 * | 7/2010 | Sato et al. | 439/281 |
| 2001/0051774 A1 | 12/2001 | Littrup et al. | |
| 2002/0109621 A1 | 8/2002 | Khair et al. | |
| 2002/0138019 A1 | 9/2002 | Wexler et al. | |
| 2003/0004403 A1 | 1/2003 | Drinan et al. | |
| 2003/0023184 A1 | 1/2003 | Pitts-crick et al. | |
| 2003/0028221 A1 | 2/2003 | Zhu et al. | |
| 2003/0105411 A1 | 6/2003 | Smallwood et al. | |
| 2003/0120170 A1 | 6/2003 | Zhu et al. | |
| 2003/0120182 A1 | 6/2003 | Wilkinson et al. | |
| 2003/0173976 A1 | 9/2003 | Wiegand et al. | |
| 2003/0216664 A1 | 11/2003 | Suarez | |
| 2004/0015095 A1 | 1/2004 | Li et al. | |
| 2004/0019292 A1 | 1/2004 | Drinan et al. | |
| 2004/0073127 A1 | 4/2004 | Istvan et al. | |
| 2004/0073130 A1 | 4/2004 | Bohm et al. | |
| 2004/0116819 A1 | 6/2004 | Alt et al. | |
| 2004/0158167 A1 | 8/2004 | Smith et al. | |
| 2004/0167423 A1 | 8/2004 | Pillon et al. | |
| 2004/0234113 A1 | 11/2004 | Miga | |
| 2004/0236202 A1 | 11/2004 | Burton | |
| 2004/0242989 A1 | 12/2004 | Zhu et al. | |
| 2004/0253652 A1 | 12/2004 | Davies | |
| 2004/0260167 A1 | 12/2004 | Leonhardt et al. | |
| 2004/0267344 A1 | 12/2004 | Stett et al. | |
| 2005/0039763 A1 | 2/2005 | Kraemer et al. | |
| 2005/0070778 A1 | 3/2005 | Lackey et al. | |
| 2005/0080460 A1 | 4/2005 | Wang et al. | |
| 2005/0101875 A1 | 5/2005 | Semler et al. | |
| 2005/0107719 A1 | 5/2005 | Arad | |
| 2005/0177062 A1 | 8/2005 | Skrabal et al. | |
| 2005/0192488 A1 | 9/2005 | Bryenton et al. | |
| 2005/0201598 A1 | 9/2005 | Harel et al. | |
| 2005/0203435 A1 | 9/2005 | Nakada | |
| 2005/0215918 A1 | 9/2005 | Frantz et al. | |
| 2005/0228309 A1 | 10/2005 | Fisher | |
| 2005/0251004 A1 * | 11/2005 | Istvan et al. | 600/395 |
| 2005/0261743 A1 | 11/2005 | Kroll et al. | |
| 2005/0283091 A1 | 12/2005 | Kink et al. | |
| 2006/0004300 A1 | 1/2006 | Kennedy | |
| 2006/0041280 A1 | 2/2006 | Stahmann et al. | |
| 2006/0064029 A1 | 3/2006 | Arad | |
| 2006/0085049 A1 | 4/2006 | Cory et al. | |
| 2006/0122540 A1 | 6/2006 | Zhu et al. | |
| 2006/0135886 A1 | 6/2006 | Lippert et al. | |
| 2006/0200033 A1 | 9/2006 | Keren et al. | |
| 2006/0224079 A1 | 10/2006 | Washchuk | |
| 2006/0241513 A1 | 10/2006 | Hatlestad et al. | |
| 2006/0241719 A1 | 10/2006 | Foster et al. | |
| 2006/0247543 A1 | 11/2006 | Cornish et al. | |
| 2006/0258952 A1 | 11/2006 | Stahmann et al. | |
| 2006/0264775 A1 | 11/2006 | Mills et al. | |
| 2006/0264776 A1 | 11/2006 | Stahmann et al. | |
| 2006/0293609 A1 | 12/2006 | Stahmann et al. | |
| 2007/0007975 A1 | 1/2007 | Hawkins et al. | |
| 2007/0010758 A1 | 1/2007 | Matthiessen et al. | |
| 2007/0027402 A1 | 2/2007 | Levin et al. | |
| 2007/0049993 A1 | 3/2007 | Hofmann et al. | |
| 2007/0156061 A1 | 7/2007 | Hess | |
| 2008/0001608 A1 | 1/2008 | Saulnier et al. | |
| 2008/0064981 A1 | 3/2008 | Gregory | |
| 2008/0188757 A1 | 8/2008 | Rovira et al. | |
| 2008/0252304 A1 | 10/2008 | Woo et al. | |
| 2008/0319336 A1 | 12/2008 | Ward et al. | |
| 2009/0054952 A1 * | 2/2009 | Glukhovsky et al. | 607/61 |
| 2009/0084674 A1 | 4/2009 | Holzhacker et al. | |
| 2011/0118619 A1 | 5/2011 | Burton et al. | |

FOREIGN PATENT DOCUMENTS

| | | |
|---|---|---|
| CN | 1236597 A | 12/1999 |
| CN | 1329875 A | 1/2002 |
| EP | 0581073 A2 | 2/1994 |
| EP | 0339471 B1 | 3/1997 |
| EP | 0865763 A2 | 9/1998 |
| EP | 1078597 A2 | 2/2001 |
| EP | 1112715 A1 | 7/2001 |

(56) References Cited

FOREIGN PATENT DOCUMENTS

| | | |
|---|---|---|
| EP | 1238630 A2 | 9/2002 |
| EP | 1247487 A1 | 10/2002 |
| EP | 1329190 A1 | 7/2003 |
| EP | 1080686 B1 | 3/2004 |
| FR | 2748928 A1 | 11/1997 |
| JP | 06-000168 A | 1/1994 |
| JP | 08-191808 A | 7/1996 |
| JP | 09-051884 A | 2/1997 |
| JP | 09-220209 A | 8/1997 |
| JP | 10-000185 A | 1/1998 |
| JP | 2002502274 | 10/1998 |
| JP | 2000-107138 A | 4/2000 |
| JP | 2000-139867 A | 5/2000 |
| JP | 2001037735 A | 2/2001 |
| JP | 2001061804 A | 3/2001 |
| JP | 2001-224568 A | 8/2001 |
| JP | 2003-2116805 A | 4/2003 |
| JP | 2003-230547 A | 8/2003 |
| JP | 2004-61251 A | 2/2004 |
| JP | 2005-137683 | 6/2005 |
| NL | 1019789 C2 | 7/2003 |
| RU | 2112416 C1 | 6/1998 |
| RU | 2138193 C1 | 9/1999 |
| WO | WO 93/18821 A1 | 9/1993 |
| WO | WO 94/01040 A1 | 1/1994 |
| WO | WO 94/10922 A1 | 5/1994 |
| WO | WO 96/01586 A1 | 1/1996 |
| WO | WO 97/11638 A2 | 4/1997 |
| WO | WO 98/06328 A1 | 2/1998 |
| WO | WO98/33553 A1 | 8/1998 |
| WO | WO 98/51211 A1 | 11/1998 |
| WO | WO 00/19886 A1 | 4/2000 |
| WO | WO 00/40955 A1 | 7/2000 |
| WO | WO00/79255 A1 | 12/2000 |
| WO | WO 01/27605 A1 | 4/2001 |
| WO | 02-53028 A2 | 7/2002 |
| WO | 2004-032738 A1 | 4/2004 |
| WO | WO 2004/030535 A1 | 4/2004 |
| WO | WO 2004/032738 A1 | 4/2004 |
| WO | 2004-043252 A1 | 5/2004 |
| WO | 2004-047636 A1 | 6/2004 |
| WO | WO 2004/047638 A1 | 6/2004 |
| WO | WO 2004/084087 A1 | 9/2004 |
| WO | 2004-098389 A2 | 11/2004 |
| WO | WO 2005/018432 A2 | 3/2005 |
| WO | WO 2005/122881 A1 | 12/2005 |
| WO | WO 2005/122888 A1 | 12/2005 |
| WO | 2007-056493 A1 | 5/2007 |

OTHER PUBLICATIONS

Chetham, Matthew; U.S. Appl. No. 11/776,456 entitled "Cardiac monitoring system," filed Jul. 11, 2007.

Chetham, Matthew; U.S. Appl. No. 11/996,065 entitled "Index determination," filed Jan. 19, 2008.

Bella et al., "Relations of left ventrical mass to fat-free and adipose body mass: the strong heart study," Circulation, vol. 98, pp. 2538-2544, Dec. 8, 1998.

Ellis, K.J. et al., "Human hydrometry: comparison of multifrequency bioelectrical impedance with 2H2O and bromine dilution," Journal of Applied Physiology, vol. 85, No. 3, pp. 1056-1062, 1998.

Iacobellis et al., "Influence of excess fat on cardiac morphology and function: study in uncomplicated obesity," Obesity Research, vol. 10, No. 8, pp. 767-773, Aug. 8, 2002.

Jones, C.H. et al., "Extracellular fluid volume determined by bioelectric impedance and serum albumin in CAPD Patients," Nephrology Dialysis Transplantation, vol. 13, pp. 393-397, 1998.

Thomas, B.J., "Future Technologies," Asia Pacific Journal Clinical Nutrition, vol. 4, pp. 157-159, 1995.

Woodrow, G. et al., "Effects of icodextrin in automated peritoneal dialysis on blood pressure and bioelectrical impedance analysis," Nephrology Dialysis Transplantation, vol. 15, pp. 862-866, 2000.

Yoshinaga et al., "Effect of total adipose weight and systemic hypertension on left ventrical mass in children," American Journal of Cardiology, vol. 76, pp. 785-787, Oct. 15, 1995.

Karason et al., "Impact of blood pressure and insulin on the relationship between body fat and left ventricular structure," European Heart Journal, vol. 24, pp. 1500-1505, 2003.

Bernstein; "A new stroke volume equation for thoracic electrical bio impedance," Critical Care Medicine; 1986; vol. 14; pp. 904-909.

Thomas, et al.; "Bioimpedance spectrometer in the determination of body water compartments: Accuracy and clinical significance;" Appl. Radiation. Isotopes; vol. 49, No. 5/6; pp. 447-455; 1998.

Chetham, Scott; U.S. Appl. No. 12/090,078 entitled "Hydration status monitoring," filed Apr. 11, 2008.

Chetham, Scott M.,; U.S. Appl. No. 13/305,606 entitled "Cardiac monitoring system" filed Nov. 28, 2011.

McAdams et al.; Tissue impedance: a historical overview; Physiological Measurement, Institute of Physics Publishing, Bristol, GB; 16 (3A); pp. A1-A13; Aug. 1, 1995.

* cited by examiner

APPARATUS FOR CONNECTING IMPEDANCE MEASUREMENT APPARATUS TO AN ELECTRODE

RELATED APPLICATIONS

This application is a U.S. National Phase under 35 U.S.C. §371 of the International Patent Application No. PCT/AU06/00923, filed Jun. 3, 2006, and published in English on Jan. 11, 2007 as WO 2007/002992, which claims the benefit of each of U.S. Provisional Patent Application No. 60/697,100, filed Jul. 7, 2005, U.S. Provisional Patent Application No. 60/703,270, filed Jul. 28, 2005, Australian Patent Application No. 2005903510, filed Jul. 1, 2005 and Australian Patent Application No. 2005903887, filed Jul. 20, 2005, all of which are incorporated by reference in their entirety.

BACKGROUND OF THE INVENTION

The present invention relates to a method and apparatus for monitoring biological parameters, and in particular to a method and apparatus for performing impedance measurements to determine the presence, absence or degree of pulmonary oedema.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

The clinical management of heart failure consumes approximately 1% to 2% of the health care budget in developed countries, with the majority of this expense due to costs associated with hospitalisation. A pan-European survey has shown that up to 65% of patients who are hospitalised for clinical heart failure have had previous admissions for such a condition. Typically admission for clinical heart failure lasts for an average of 11 days with a risk of re-hospitalisation of 24%.

One of the major risks associated with congestive heart failure is the development of pulmonary oedema, which is caused by the extravascular accumulation of fluid in the pulmonary tissue and air spaces. Whilst this is a serious problem, and can have fatal consequences if not correctly treated, treatment is relatively straightforward and typically involves the use of diuretics to reduce fluid levels.

However, assessment and monitoring of pulmonary oedema is a complex process. In particular current techniques typically involve ionising radiation or invasive methods, and accordingly, such processes can only be performed under adequate medical supervision. For home monitoring of pulmonary oedema or the extent of congestive heart failure (CHF), the current clinically accepted methodology is for the patient to weigh themselves in the morning following their morning absolutions. If their weight has changed by a significant factor since their last measurement they are advised to call their physician. Physicians rely on subjective assessment of exercise tolerance and breathlessness, changes in body weight and clinical examination to detect increasing dependent oedema or lung crackles.

Other methods have been proposed for the accurate measurement of assessing heart failure ranging from the use of implantable devices for hemodynamic monitoring, implantable intra-thoracic impedance monitors and serial measurements of B-type natriuretic peptide. Implantable devices are not suitable for the general population and have all the associated risk factors that arise from such systems, whilst B-type natriuretic peptide monitoring is restricted to major health care centres and is not practical for home monitoring.

Accordingly, in many cases, onset or progression of pulmonary oedema is not detected until the patient is admitted to hospital. The patient is then often required to remain in hospital whilst treatment is provided, to allow adequate monitoring of the patient's recovery. However, if adequate diagnosis and monitoring techniques were available many of such hospital visits could be avoided thereby vastly reducing the burden on the health care system.

One existing technique for determining biological parameters relating to a subject involves the use of bioelectrical impedance. This involves measuring the electrical impedance of a subject's body using a series of electrodes placed on the skin surface. Changes in electrical impedance at the body's surface are used to determine parameters, such as changes in fluid levels.

A complication in such techniques is that the baseline impedance of the thorax varies considerably between individuals, the quoted range for an adult is $20\Omega$-$48\Omega$ at a frequency between 50 kHz-100 kHz, and variations in impedance due to changes in fluid level can be quite small. This leads to a very fragile signal with a low signal to noise ratio. As a result these techniques have not been suitable for monitoring pulmonary oedema, other than through invasive techniques, which as discussed above do not provide a suitable mechanism for monitoring patients in most cases.

SUMMARY OF THE PRESENT INVENTION

In a first broad form the present invention provides a method of monitoring pulmonary oedema in a subject, the method including, in a processing system:
  a) determining a measured impedance value for at least two body segments, at least one of the body segments being a thoracic cavity segment;
  b) for each body segment, and using the measured impedance values, determining an index; and,
  c) determining the presence, absence or degree of pulmonary oedema using the determined indices.

Typically the index is of a ratio of the extra-cellular to intracellular fluid.

Typically the method includes, in the processing system:
  a) comparing the indices of the body segments; and,
  b) determining the presence, absence or degree of pulmonary oedema using the results of the comparison.

Typically the method includes, in the processing system:
  a) determining an index ratio based on a ratio of the indices;
  b) comparing the index ratio to at least one reference; and,
  c) determining the presence, absence or degree of pulmonary oedema using the results of the comparison.

Typically the reference includes at least one of:
  a) a predetermined threshold;
  b) a tolerance determined from a normal population; and,
  c) a predetermined range.

Typically the reference includes an index ratio previously determined for the subject.

Typically the method includes, in the processing system:
  a) determining a plurality of measured impedance values for each body segment, each measured impedance value being measured at a corresponding measurement frequency; and, b) determining the index ratio based on the plurality of measured impedance values.

Typically the method includes, in the processing system, and for each body segment:
a) determining values for parameters $R_0$ and $R_\infty$ from the measured impedance values; and,
b) calculating the index (I) using the equation:

$$I = \frac{R_\infty}{R_0 - R_\infty}$$

where:
$R_0$ is the resistance at zero frequency; and,
$R_\infty$ is the resistance at infinite frequency.

Typically the method includes, in the processing system, determining the parameter values using the equation:

$$Z = R_\infty + \frac{R_0 - R_\infty}{1 + (j\omega\tau)^{(1-\alpha)}}$$

where:
Z is the measured impedance at angular frequency $\omega$,
$\tau$ is a time constant, and
$\alpha$ has a value between 0 and 1.

Typically the method includes, in the processing system:
a) determining the impedance of each body segment at four discrete frequencies; and,
b) determining values for the parameters by solving the equation using four simultaneous equations.

Typically the method includes, in the processing system, determining the parameter values by:
a) determining an impedance locus using the measured impedance values; and,
b) using the impedance locus to determine the parameter values.

Typically the thoracic cavity segment corresponds to the entire thoracic cavity.

Typically wherein the other body segment is at least one other thoracic cavity segment.

Typically the at least one other body segment is a limb.

Typically the method includes, in the processing system, determining if the at least one other body segment suffers from oedema.

Typically the method includes, in the processing system:
a) determining, using measured impedance values, the impedance of the entire subject and each limb; and,
b) subtracting the limb impedance values from the entire subject impedance values to determine the impedance of the thoracic cavity.

Typically the method includes, in the processing system:
a) causing one or more electrical signals to be applied to the subject using a first set of electrodes, the one or more electrical signals having a plurality of frequencies;
b) determining an indication of electrical signals measured across a second set of electrodes applied to the subject in response to the applied one or more signals;
c) determining from the indication and the one or more applied signals, an instantaneous impedance value at each of the plurality of frequencies; and,
d) determining the index using the instantaneous impedance values.

Typically a number of electrodes are provided on the subject's thoracic cavity, and wherein the method includes, in the processing system:
a) causing one or more electrical signals to be applied to a pair of the electrodes;
b) determining an indication of electrical signals measured across each other pair of electrodes;
c) determining from the indication and the one or more applied signals, an instantaneous impedance value for at least one thoracic cavity segment; and,
d) repeating steps a) to c) by applying electrical signals to each other pair of the electrodes to thereby determine impedance values for a number of thoracic cavity segments.

Typically the method includes, in the processing system:
a) determining at least one impedance measurement to be performed;
b) determining at least one electrode arrangement associated with the determined impedance measurement;
c) displaying a representation indicative of the electrode arrangement; and,
d) causing the impedance measurement to be performed once the electrodes have been provided in accordance with the displayed representation.

Typically the method includes, in the computer system, displaying an indication of at least one of:
a) the parameter values;
b) the ratio of extra-cellular to intra-cellular fluid; and,
c) an indication of the at least one of the presence, absence or degree of tissue oedema in the subject.

Typically the method includes, in the processing system:
a) determining an electrode identifier associated with at least one electrode provided on the subject;
b) determining, using the electrode identifier, an electrode position indicative of the position of the at least one electrode on the subject; and,
c) performing at least one impedance measurement using the electrode position.

Typically the method includes, in the processing system:
a) determining a parameter associated with at least one electrode lead; and,
b) causing at least one impedance measurement to be performed using the determined parameter.

Typically the method includes, in the processing system:
a) receiving configuration data, the configuration data being indicative of at least one feature;
b) determining, using the configuration data, instructions representing the at least one feature; and,
c) causing, using the instructions, at least one of.
  i) at least one impedance measurement to be performed; and,
  ii) at least one impedance measurement to be analysed.

Typically the method includes, in the processing system:
a) causing a first signal to be applied to the subject;
b) determining at least one parameter relating to at least one second signal measured across the subject,
c) comparing the at least one parameter to at least one threshold; and,
d) depending on the results of the comparison, selectively repeating steps (a) to (d) using a first signal having an increased magnitude.

In a second broad form the present invention provides apparatus for monitoring pulmonary oedema in a subject, the apparatus including a processing system for:
a) determining a measured impedance value for at least two body segments, at least one of the body segments being a thoracic cavity segment;
b) for each body segment, and using the measured impedance values, determining an index; and, c) determining the presence, absence or degree of pulmonary oedema using the determined indices.

Typically the apparatus includes:
a) a current supply for generating an alternating current at each of a plurality of frequencies;
b) at least two supply electrodes for applying the generated alternating current to a subject;
c) at least two measurement electrodes for detecting a voltage across the subject; and,
d) a sensor coupled to the measurement electrodes for determining the voltage, the sensor being coupled to the processing system to thereby allow the processing system to determine the measured impedances.

Typically the apparatus includes a number of electrodes arranged in a band for fitting to the subject's thoracic cavity.

Typically the apparatus includes a multiplexing system for selectively coupling the current supply and the sensor to the number of electrodes in a predetermined sequence.

In a third broad form the present invention provides a method of diagnosing a presence, absence or degree of pulmonary oedema in a subject, the method including, in a processing system:
a) determining a measured impedance value for at least two body segments, at least one of the body segments being a thoracic cavity segment;
b) for each body segment, and using the measured impedance values, determining an index; and,
c) determining the presence, absence or degree of pulmonary oedema using the determined indices.

In a fourth broad form the present invention provides apparatus for connecting measurement apparatus to an electrode, the apparatus including:
a) a housing having a connector for coupling the housing to an electrode; and,
b) a circuit mounted in the housing, the circuit being electrically coupled to the electrode using the connector, and being coupled to a lead, the circuit being for at least one of:
  i) generating predetermined electrical signals in accordance with control signals received from the measurement apparatus;
  ii) providing an indication of electrical signals applied to the electrode; and,
  iii) providing an indication of electrical signals measured at the electrode.

Typically the circuit is provided on a circuit board having an electrical contact, and wherein in use the connector urges at least part of the electrode into abutment with the electrical contact.

Typically the connector includes a biased arm.

Typically the circuit includes a buffer circuit for:
a) sensing voltage signals at the electrode;
b) filtering and amplifying the voltage signals; and,
c) transferring the filtered and amplified voltage signals to the measurement apparatus.

Typically the circuit includes a current source circuit for:
a) receiving one or more control signals;
b) filtering and amplifying the control signals to thereby generate one or more current signals;
c) applying the current signals to the electrode pad; and,
d) transferring an indication of the applied signals to the measurement apparatus.

Typically the apparatus further comprises an electrode, the electrode including:
a) an electrode substrate; and,
b) a conductive material for electrically coupling the electrode to the subject.

Typically the electrode substrate is electrically conductive, and wherein in use the connector couples the circuit to the electrode substrate.

Typically the housing includes curved edges.

Typically the housing is formed from a material that, at least one of:
a) has a low coefficient of friction; and,
b) is resilient.

In a fifth broad form the present invention provides a method of performing impedance measurements on a subject, the method including, in a processing system:
a) determining an encoded value associated with at least one electrode lead; and,
b) causing at least one impedance measurement to be performed using the encoded value.

Typically the encoded value is used for calibration.

Typically the encoded value is determined from a resistance value.

Typically the encoded value is indicative of an identity of the lead.

Typically the method includes, in the processing system, controlling the current applied to the subject using the determined encoded value.

Typically the encoded value is a lead identifier, and wherein the method includes, in the processing system:
a) determining, using the lead identifier, an impedance measurement procedure; and,
b) causing the determined impedance measurement procedure to be performed.

Typically the method includes, in the processing system:
a) comparing the determined identity to one or more predetermined identities; and,
b) determining the impedance of the subject in response to a successful comparison.

Typically the method includes, in the processing system:
a) determining the lead identifier associated with the at least one electrode lead;
b) determining, using the lead identifier, a lead usage;
c) comparing the lead usage to a threshold; and,
d) in accordance with the results of the comparison, at least one of:
  i) generating an alert;
  ii) terminating an impedance measurement procedure; and,
  iii) performing an impedance measurement procedure.

Typically the method includes, in the processing system, at least one of:
a) processing electrical signals measured from the subject to thereby determine one or more impedance values; and,
b) processing determined impedance values.

Typically the encoded value is stored in a store.

In a fifth broad form the present invention provides apparatus for performing impedance measurements on a subject, the apparatus including:
a) at least one lead for connecting to electrodes coupled to the subject, the at least one lead including an encoded value; and,
b) a processing system coupled to the at least one lead for:
  i) determining the encoded value; and,
c) causing at least one impedance measurement to be performed using the encoded value.

In a sixth broad form the present invention provides a method of performing impedance measurements on a subject, the method including, in a processing system:
a) determining an electrode identifier associated with at least one electrode provided on the subject, b) determining, using the electrode identifier, an electrode position indicative of the position of the at least one electrode on the subject; and, c) causing at least one impedance measurement to be performed using the electrode position.

Typically the impedance measurement is performed using at least four electrodes, each having a respective identifier, and wherein the method includes, in the processing system:

a) determining an electrode identifier for each electrode;

b) determining, using each electrode identifier, an electrode position for each electrode; and, c) performing at least one impedance measurement using the electrode positions.

Typically the method includes, in the processing system:

a) causing signals to be applied to at least two of the electrodes in accordance with the determined electrode positions; and, b) causing signals to be measured from at least two of the electrodes in accordance with the determined electrode positions.

Typically the method includes, in the processing system, determining the electrode identifier for an electrode by selectively measuring the conductivity between one or more contacts provided on the electrode.

Typically the processing system is coupled to a signal generator and a sensor, and wherein the method includes, in the processing system:

a) selectively interconnecting the signal generator and at least two electrode leads, to thereby allow signals to be applied to the subject; and, b) selectively interconnecting the sensor at least two electrode leads to thereby allow a signal to be measured from the subject.

Typically the method includes, in the processing system controlling a multiplexer to thereby selectively interconnect the leads and at least one of the signal generator and the sensor.

Typically the at least one electrode includes visual indicia indicative of the position of the at least one electrode on the subject.

In a seventh broad form the present invention provides apparatus for performing impedance measurements on a subject, the apparatus including a processing system for:

a) determining an electrode identifier associated with at least one electrode provided on the subject;

b) determining, using the electrode identifier, an electrode position indicative of the position of the at least one electrode on the subject; and, c) causing at least one impedance measurement to be performed using the electrode position.

In an eighth broad form the present invention provides a method of performing impedance measurements on a subject, wherein the method includes, in a processing system:

a) causing a first signal to be applied to the subject;

b) determining at least one parameter relating to at least one second signal measured across the subject, c) comparing the at least one parameter to at least one threshold; and, d) depending on the results of the comparison, selectively repeating steps (a) to (d) using a first signal having an increased magnitude.

Typically the method includes, in the processing system:

a) determining an animal type of the subject; and, b) selecting the threshold in accordance with the animal type.

Typically the threshold is indicative of at least one of:

a) a minimum second signal magnitude; and, b) a minimum signal to noise ratio for the second signal.

Typically the method includes, in the processing system:

a) determining at least one parameter relating to the at least one first signal;

b) comparing the at least one parameter to at least one threshold; and, c) selectively terminating impedance measurements depending on the results of the comparison.

Typically the threshold is indicative of a maximum first signal magnitude.

In a ninth broad form the present invention provides apparatus for performing impedance measurements on a subject, wherein the apparatus includes a processing system for:

a) causing a first signal to be applied to the subject;

b) determining at least one parameter relating to at least one second signal measured across the subject;

c) comparing the at least one parameter to at least one threshold; and, d) depending on the results of the comparison, selectively repeating steps (a) to (d) using a first signal having an increased magnitude.

Typically the apparatus further includes a variable magnitude current supply.

In a tenth broad form the present invention provides a method of providing an electrode for use in impedance measurement procedures, the method including:

a) providing on a substrate:
   i) a number of electrically conductive contact pads; and,
   ii) a corresponding number of electrically conductive tracks, each track extending from an edge of the substrate to a respective contact pad;

b) applying an insulating layer to the substrate, the insulating layer including a number of apertures, and being positioned to thereby overlay the tracks with at least a portion of each pad contact aligned with a respective aperture; and, c) providing an electrically conductive medium in the apertures.

Typically the electrically conductive medium is formed from a conductive gel.

Typically the conductive gel is silver/silver chloride gel.

Typically the method includes, providing a covering layer on the insulating layer to thereby cover the electrically conductive medium.

Typically the insulating layer has an adhesive surface that releasably engages the covering layer.

Typically the substrate is an elongate substrate, and wherein the method includes aligning the pad contacts along the length of the substrate.

Typically the method includes providing the tracks and contact pads using at least one of:

a) screen printing;

b) inkjet printing; and, c) vapour deposition.

Typically the tracks and contact pads are formed from silver.

Typically the method includes forming the substrate by:

a) overlaying a plastic polymer with a shielding material; and, b) covering the shielding material with an insulating material.

In an eleventh broad form the present invention provides an electrode for use in impedance measurement procedures, the electrode including:

a) a substrate having provided thereon:
   i) a number of electrically conductive contact pads; and,
   ii) a corresponding number of electrically conductive tracks, each track extending from an edge of the substrate to a respective contact pad;
b) an insulating layer provided on the substrate, the insulating layer including a number of apertures, and being positioned to thereby overlay the tracks with at least a portion of each pad contact aligned with a respective aperture; and,
c) an electrically conductive medium provided in the apertures.

In a twelfth broad form the present invention provides a method for use in diagnosing conditions in a subject, the method including, in a processing system:
a) determining an encoded value associated with at least one electrode lead; and,
b) causing at least one impedance measurement to be performed using the encoded value.

In a thirteenth broad form the present invention provides a method for use in diagnosing conditions in a subject, the method including, in a processing system:
a) determining an electrode identifier associated with at least one electrode provided on the subject;
b) determining, using the electrode identifier, an electrode position indicative of the position of the at least one electrode on the subject; and,
c) causing at least one impedance measurement to be performed using the electrode position.

In a fourteenth broad form the present invention provides a method for use in diagnosing conditions in a subject, the method including, in a processing system:
a) receiving configuration data, the configuration data being indicative of at least one feature;
b) determining, using the configuration data, instructions representing the at least one feature; and,
c) causing the measuring device to perform, using the instructions, at least one of:
   i) impedance measurements; and,
   ii) analysis of impedance measurements.

In a fifteenth broad form the present invention provides a method for use in diagnosing conditions in a subject, the method including, in a processing system:
a) determining configuration data required for a measuring device, the configuration data being indicative of at least one feature; and,
b) causing the configuration data to be received by a processing system in the measuring device, the processing system being responsive to the configuration data to configure the measuring device to allow the at least one feature to be used.

In a sixteenth broad form the present invention provides a method for use in diagnosing conditions in a subject, the method including, in a processing system:
a) causing a first signal to be applied to the subject;
b) determining at least one parameter relating to at least one second signal measured across the subject;
c) comparing the at least one parameter to at least one threshold; and,
d) depending on the results of the comparison, selectively repeating steps (a) to (d) using a first signal having an increased magnitude.

In a seventeenth broad form the present invention provides a method for configuring a processing system for use in impedance analysis of a subject, the method including, in a processing system:

a) receiving configuration data, the configuration data being indicative of at least one feature;
b) determining, using the configuration data, instructions representing the at least one feature; and,
c) causing, at least in part using the instructions, at least one of:
   i) impedance measurements to be performed; and,
   ii) analysis of impedance measurements.

Typically the configuration data includes the instructions.
Typically the method includes, in the processing system:
a) determining an indication of the at least one feature using the configuration data; and,
b) determining the instructions using the indication of the at least one feature.

Typically the method includes, in the processing system, decrypting the received configuration data.

Typically the method includes, in the processing system:
a) determining a device identifier associated with the processing system;
b) determining, using the device identifier, a key; and,
c) decrypting the received configuration data using the key.

Typically the processing system includes first and second processing systems, and wherein the method includes:
a) in the first processing system, selecting the instructions using the configuration data; and,
b) in the second processing system, generating the control signals using selected instructions.

Typically the method includes, in the processing first system, at least one of:
a) transferring the instructions to the second processing system; and,
b) causing the second processing system to access the instructions from a store.

Typically the method includes, in the processing system, receiving the configuration data from at least one of a computer system and a communications network.

Typically the method includes, in the processing system:
a) determining if a feature selected by a user is available;
b) if the feature is not available, determining if the user wishes to enable the feature; and,
c) if the user wishes to enable the feature, causing configuration data to be received.

Typically the method includes, in the processing system:
a) causing the user to provide a payment to a device provider; and,
b) receiving the configuration data in response to payment.

In an eighteenth broad form the present invention provides apparatus for configuring a processing system for use in impedance analysis of a subject, the apparatus including a processing system for:
a) receiving configuration data, the configuration data being indicative of at least one feature;
b) determining, using the configuration data, instructions representing the at least one feature; and,
c) causing, at least in part using the instructions, at least one of:
   i) impedance measurements to be performed; and,
   ii) analysis of impedance measurements.

Typically the processing system forms at least part of at least one of:
a) an end station; and,
b) a measuring device.

In a nineteenth broad form the present invention provides a method for configuring a processing system for use in impedance analysis of a subject, the method including, in a computer system:

a) determining configuration data required for the processing system, the configuration data being indicative of at least one feature; and,
b) causing the configuration data to be received by the processing system being responsive to the configuration data to cause, at least one of:
   i) impedance measurements to be performed; and,
   ii) analysis of impedance measurements.

Typically the method includes, in the computer system:
a) determining a device identifier, the device identifier being associated with the processing system to be configured; and,
b) using the device identifier to at least one of:
   i) transfer the configuration data to the processing system; and,
   ii) encrypt the configuration data.

Typically the method includes, in the computer system, determining the configuration data is required in response to at least one of:
a) payment made by a user of the processing system; and,
b) approval of the feature.

Typically the method includes, in the computer system:
a) determining regulatory approval of the at least one feature in at least one region;
b) determining at least one processing system in the at least one region; and,
c) configuring the at least one processing system.

In a twentieth broad form the present invention provides apparatus for configuring a processing system for use impedance analysis of a subject, the method including, in a computer system:
a) determining configuration data required for a processing system, the configuration data being indicative of at least one feature; and,
b) causing the configuration data to be received by the processing system being responsive to the configuration data to cause, at least one of:
   i) impedance measurements to be performed; and,
   ii) analysis of impedance measurements.

It will be appreciated that the broad forms of the invention may be used individual or in combination, and may be used for diagnosis of the presence, absence or degree of a range of conditions and illnesses, including, but not limited to oedema, pulmonary oedema, lymphoedema, body composition, cardiac function, and the like.

BRIEF DESCRIPTION OF THE DRAWINGS

An example of the present invention will now be described with reference to the accompanying drawings, in which:—

FIGS. 11A and 111B are schematics of an example of an electrode connection apparatus.

DETAILED DESCRIPTION OF THE PREFERRED EMBODIMENTS

Figure 1:
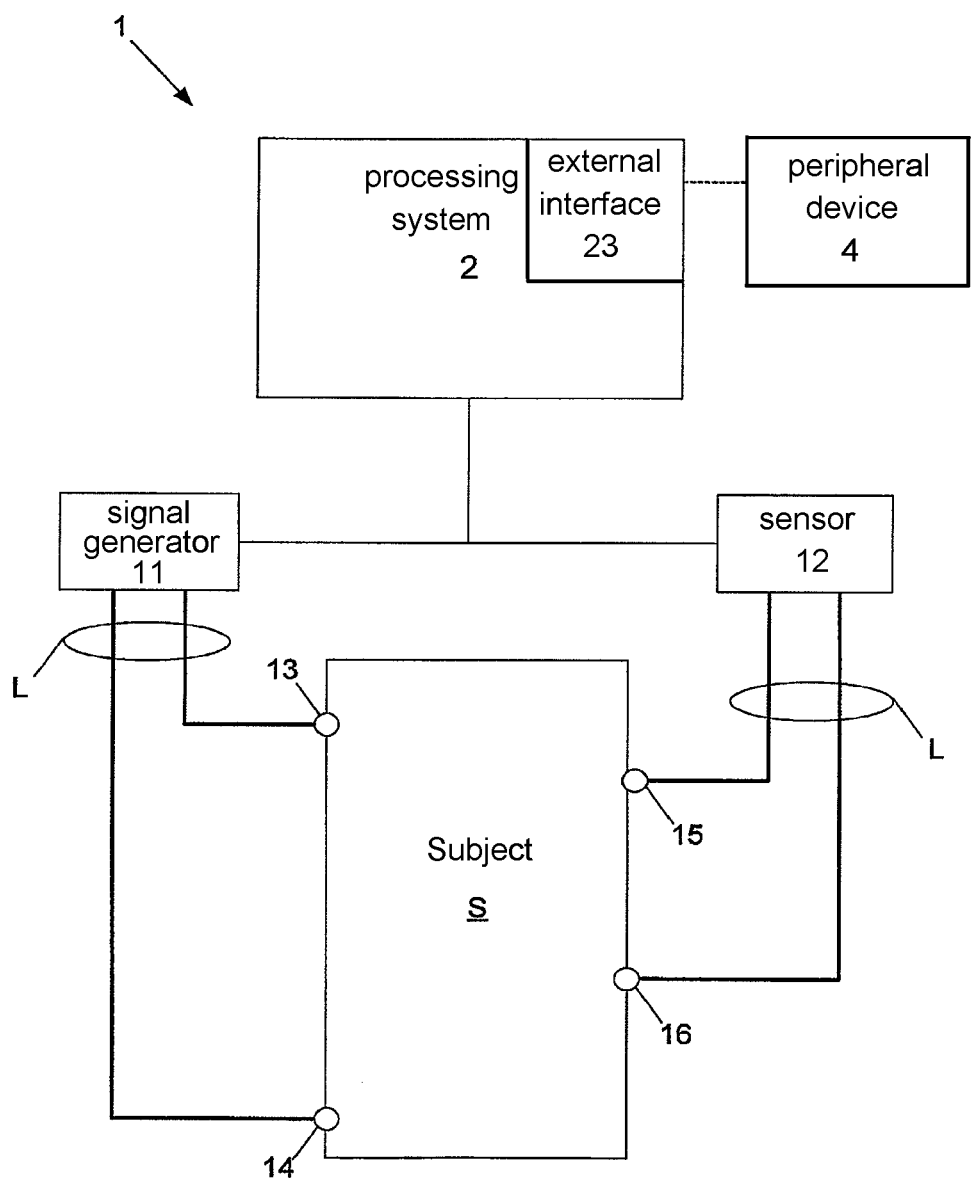
FIG. 1 is a schematic of an example of impedance determination apparatus.

An example of apparatus suitable for performing an analysis of a subject's impedance will now be described with reference to FIG. 1.

As shown the apparatus includes a measuring device 1 including a processing system 2 coupled to a signal generator 11 and a sensor 12. In use the signal generator 11 and the sensor 12 are coupled to respective electrodes 13, 14, 15, 16, provided on a subject S, via leads L, as shown. An optional external interface 23 can be used to couple the measuring device 1 to one or more peripheral devices 4, such as an external database or computer system, barcode scanner, or the like.

In use, the processing system 2 is adapted to generate control signals, which cause the signal generator 11 to generate one or more alternating signals, such as voltage or current signals, which can be applied to a subject S, via the electrodes 13, 14. The sensor 12 then determines the voltage across or current through the subject S using the electrodes 15, 16 and transfers appropriate signals to the processing system 2.

Accordingly, it will be appreciated that the processing system 2 may be any form of processing system which is suitable for generating appropriate control signals and interpreting an indication of measured signals to thereby determine the subject's bioelectrical impedance, and optionally determine other information such as cardiac parameters, or the presence absence or degree of pulmonary oedema.

The processing system 2 may therefore be a suitably programmed computer system, such as a laptop, desktop, PDA, smart phone or the like. Alternatively the processing system 2 may be formed from specialised hardware. Similarly, the I/O device may be of any suitable form such as a touch screen, a keypad and display, or the like.

It will be appreciated that the processing system 2, the signal generator 11 and the sensor 12 may be integrated into a common housing and therefore form an integrated device. Alternatively, the processing system 2 may be connected to the signal generator 11 and the sensor 12 via wired or wireless connections. This allows the processing system 2 to be provided remotely to the signal generator 11 and the sensor 12. Thus, the signal generator 11 and the sensor 12 may be provided in a unit near, or worn by the subject S, whilst the processing system 12 is situated remotely to the subject S.

In one example, the outer pair of electrodes 13, 14 are placed on the thoracic and neck region of the subject S. However, this depends on the nature of the analysis being performed. Thus, for example, whilst this electrode arrangement is suitable for cardiac function analysis, in lymphoedema, the electrodes would typically be positioned on the limbs, as required.

Once the electrodes are positioned, an alternating signal is applied to the subject S. This may be performed either by applying an alternating signal at a plurality of frequencies simultaneously, or by applying a number of alternating signals at different frequencies sequentially. The frequency range of the applied signals may also depend on the analysis being performed.

In one example, the applied signal is a frequency rich current from a current source clamped, or otherwise limited, so it does not exceed the maximum allowable subject auxiliary current. However, alternatively, voltage signals may be applied, with a current induced in the subject being measured. The signal can either be constant current, impulse function or a constant voltage signal where the current is measured so it does not exceed the maximum allowable subject auxiliary current.

A potential difference and/or current are measured between an inner pair of electrodes 15, 16. The acquired signal and the measured signal will be a superposition of potentials generated by the human body, such as the ECG, and potentials generated by the applied current.

Optionally the distance between the inner pair of electrodes may be measured and recorded. Similarly, other parameters relating to the subject may be recorded, such as the height, weight, age, sex, health status, any interventions and the date and time on which they occurred. Other information, such as current medication, may also be recorded.

To assist accurate measurement of the impedance, buffer circuits may be placed in connectors that are used to connect the voltage sensing electrodes 15, 16 to the leads L. This ensures accurate sensing of the voltage response of the subject S, and in particular helps eliminate contributions to the measured voltage due to the response of the leads L, and reduces signal loss.

This in turn greatly reduces artefacts caused by movement of the leads L, which is particularly important during dialysis as sessions usually last for several hours and the subject will move around and change positions during this time.

A further option is for the voltage to be measured differentially, meaning that the sensor used to measure the potential at each electrode 15 only needs to measure half of the potential as compared to a single ended system.

The current measurement system may also have buffers placed in the connectors between the electrodes 13, 14 and the leads L. In one example, current can also be driven or sourced through the subject S symmetrically, which again greatly reduced the parasitic capacitances by halving the common-mode current. Another particular advantage of using a symmetrical system is that the micro-electronics built into the connectors for each electrode 13, 14 also removes parasitic capacitances that arise when the subject S, and hence the leads L move.

The acquired signal is demodulated to obtain the impedance of the system at the applied frequencies. One suitable method for demodulation of superposed frequencies is to use a Fast Fourier Transform (FFT) algorithm to transform the time domain data to the frequency domain. This is typically used when the applied current signal is a superposition of applied frequencies. Another technique not requiring windowing of the measured signal is a sliding window FFT.

In the event that the applied current signals are formed from a sweep of different frequencies, then it is more typical to use a processing technique such as multiplying the measured signal with a reference sine wave and cosine wave derived from the signal generator, or with measured sine and cosine waves, and integrating over a whole number of cycles. This process rejects any harmonic responses and significantly reduces random noise.

Other suitable digital and analog demodulation techniques will be known to persons skilled in the field.

Impedance or admittance measurements are determined from the signals at each frequency by comparing the recorded voltage and current signal. The demodulation algorithm will produce an amplitude and phase signal at each frequency.

Figure 2:
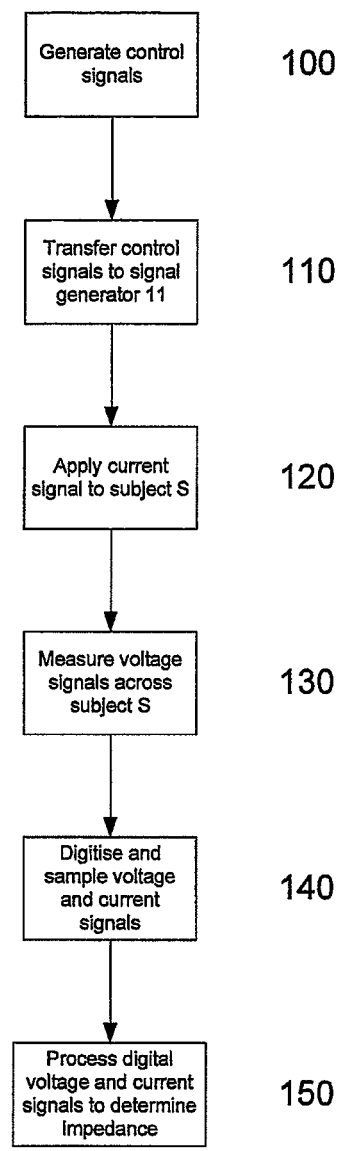
FIG. 2 is a flowchart of an example of a process for performing impedance determination.

An example of the operation of the apparatus for performing bioimpedance analysis will now be described with reference to FIG. 2.

At step 100, the processing system 2 operates to generate control signals which are provided to the signal generator 11 at step 110, thereby causing the signal generator to apply an alternating current signal to the subject S, at step 120. Typically the signal is applied at each of a number of frequencies $f_i$ to allow multiple frequency analysis to be performed.

At step 130 the sensor 12 senses voltage signals across the subject S. At step 140 the measuring device, operates to digitise and sample the voltage and current signals across the subject S, allowing these to be used to determine instantaneous bioimpedance values for the subject S at step 150.

Figure 3:
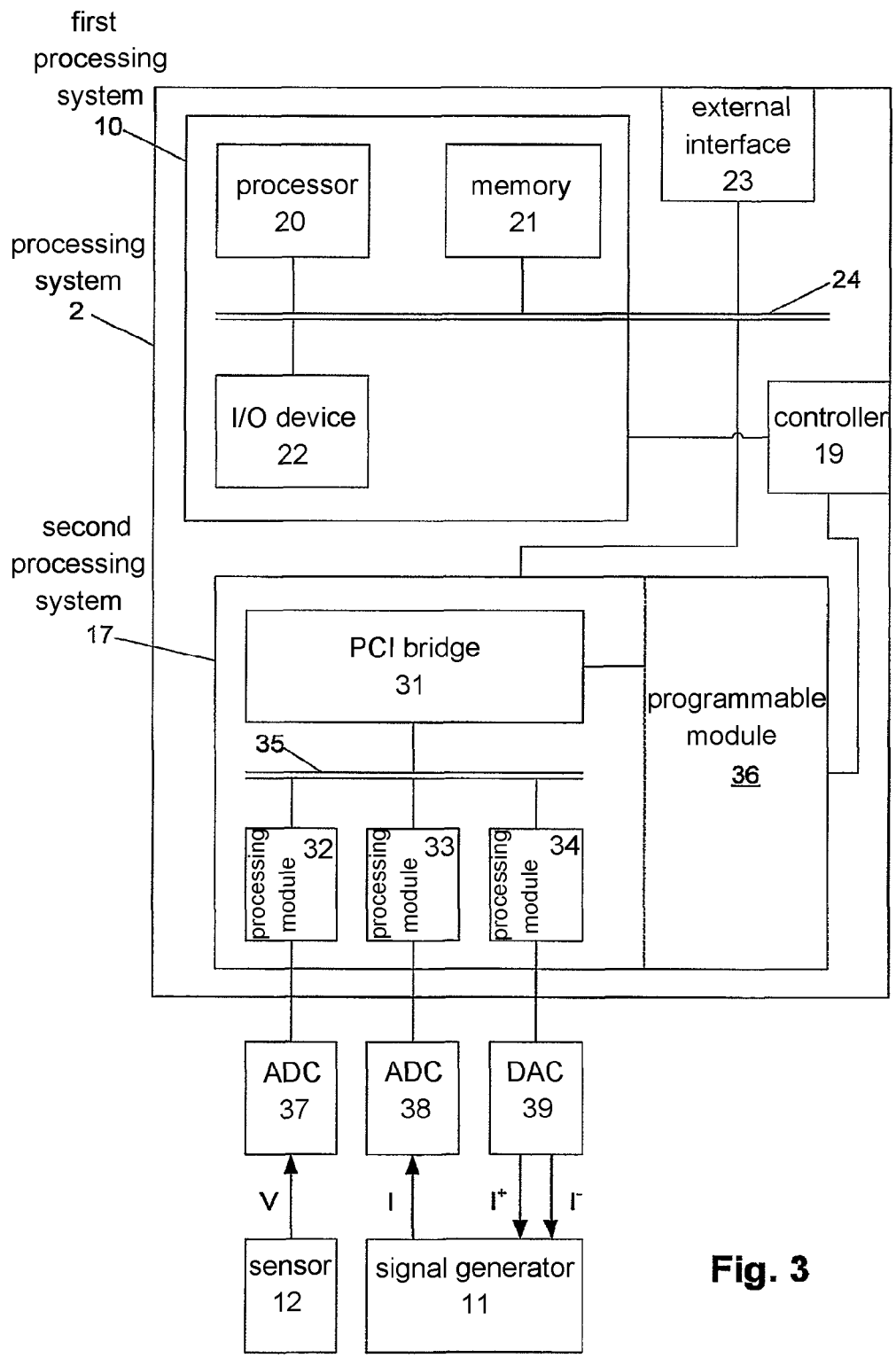
FIG. 3 is a schematic of a second example impedance determination apparatus.

A specific example of the apparatus will now be described in more detail with respect to FIG. 3.

In this example, the processing system 2 includes a first processing system 10 having a processor 20, a memory 21, an input/output (I/O) device 22, and an external interface 23, coupled together via a bus 24. The processing system 2 also includes a second processing system 17, in the form of a processing module. A controller 19, such as a micrologic controller, may also be provided to control activation of the first and second processing systems 10, 17.

In use, the first processing system 10 controls the operation of the second processing system 17 to allow different impedance measurement procedures to be implemented, whilst the second processing system 17 performs specific processing tasks, to thereby reduce processing requirements on the first processing system 10.

Thus, the generation of the control signals, as well as the processing to determine instantaneous impedance values is performed by the second processing system 17, which may therefore be formed from custom hardware, or the like. In one particular example, the second processing system 17 is formed from a Field Programmable Gate Array (FPGA), although any suitable processing module, such as a magnetologic module, may be used.

The operation of the first and second processing systems 10, 17, and the controller 19 is typically controlled using one or more sets of appropriate instructions. These could be in any suitable form, and may therefore include, software, firmware, embedded systems, or the like.

The controller 19 typically operates to detect activation of the measuring device through the use of an on/off switch (not shown). Once the controller detects device activation, the controller 19 executes predefined instructions, which in turn causes activation of the first and second processing systems 10, 17, including controlling the supply of power to the processing systems as required.

The first processing system 10 can then operate to control the instructions, such as the firmware, implemented by the second processing system 17, which in turn alters the operation of the second processing system 17. Additionally, the first processing system 10 can operate to analyse impedance determined by the second processing system 17, to allow biological parameters to be determined. Accordingly, the first processing system 10 may be formed from custom hardware or the like, executing appropriate applications software to allow the processes described in more detail below to be implemented.

It will be appreciated that this division of processing between the first processing system 10, and the second processing system 17, is not essential, but there are a number of benefits that will become apparent from the remaining description.

In this example, the second processing system 17 includes a PCI bridge 31 coupled to programmable module 36 and a bus 35, as shown. The bus 35 is in turn coupled to processing modules 32, 33, 34, which interface with ADCs (Analogue to Digital Converters) 37, 38, and a DAC (Digital to Analogue Converter) 39, respectively.

The programmable module 36 is formed from programmable hardware, the operation of which is controlled using the instructions, which are typically downloaded from the first processing system 10. The firmware that specifies the configuration of hardware 36 may reside in flash memory (not shown), in the memory 21, or may be downloaded from an external source via the external interface 23.

Alternatively, the instructions may be stored within inbuilt memory on the second processing system 17. In this example, the first processing system 10 typically selects firmware for implementation, before causing this to be implemented by the second processing system 17. This may be achieved to allow selective activation of functions encoded within the firmware, and can be performed for example using configuration data, such as a configuration file, or instructions representing applications software or firmware, or the like, as will be described in more detail below.

In either case, this allows the first processing system 10 to be used to control operation of the second processing system 17 to allow predetermined current sequences to be applied to the subject S. Thus, for example, different firmware would be utilised if the current signal is to be used to analyse the impedance at a number of frequencies simultaneously, for example, by using a current signal formed from a number of superposed frequencies, as compared to the use of current signals applied at different frequencies sequentially.

Figure 4:
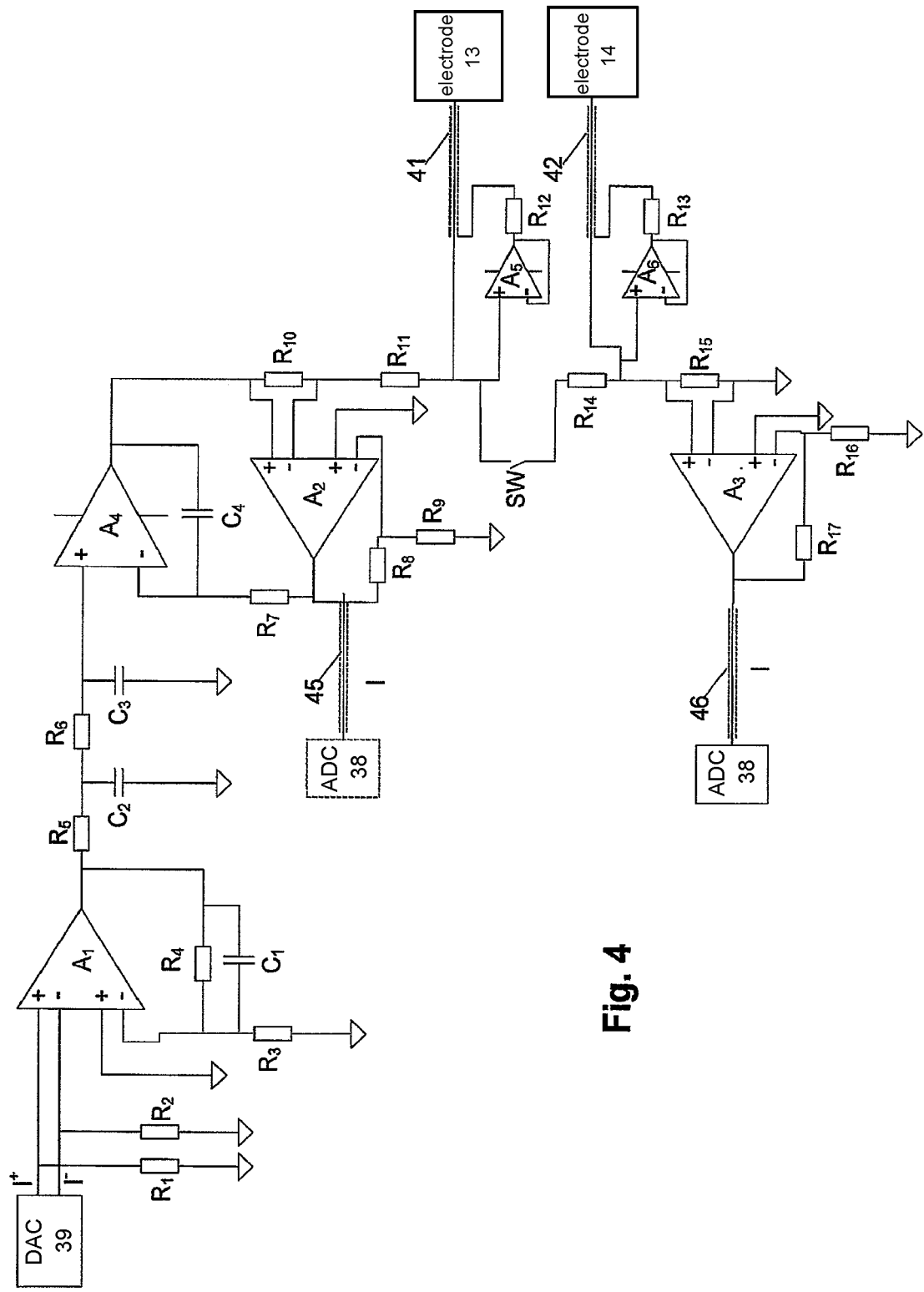
FIG. 4 is a schematic of an example of a current source circuit.

An example of a specific form of signal generator 11 in the form of a current source circuit, is shown in FIG. 4.

As shown the current source includes three fixed or variable gain differential amplifiers $A_1, A_2, A_3$ and three op-amps $A_4, A_5, A_6$, a number of resistors $R_1, \ldots R_{17}$ and capacitors $C_1, \ldots C_4$, interconnected as shown. The current source also includes leads 41, 42 (corresponding to the leads L in FIG. 1) which connect the current source to the electrodes 13, 14 and a switch SW for shorting the leads 41, 42 as will be described in more detail below.

Connections 45, 46 can also be provided for allowing the current applied to the subject S to be determined. Typically this is achieved using the connection 46. However, the connection 45 may also be used as shown in dotted lines to allow signal losses within the leads and other circuitry to be taken into account.

In general the leads used are co-axial cables with a non-braided shield and a multi strand core with a polystyrene dielectric. This provides good conductive and noise properties as well as being sufficiently flexible to avoid issues with connections from the measuring device 1 to the subject S. In this instance, resistors $R_{12}, R_{13}$ decouple the outputs of the amplifiers $A_5, A_6$ from the capacitances associated with cable.

In use, the current source circuit receives current control signals $I^+, I^-$ from the DAC 39, with these signals being filtered and amplified, to thereby form current signals that can be applied to the subject S via the electrodes 13, 14.

In use, when the amplifiers $A_1, \ldots A_6$ are initially activated, this can lead to a minor, and within safety limits, transient current surge. As the current is applied to the subject, this can result in the generation of a residual field across the subject S. To avoid this field effecting the readings, the switch SW is generally activated prior to measurements being taken, to short the current circuit, and thereby discharge any residual field.

Once the measurement is commenced, an indication of the current applied to the subject can be obtained via either one of the connections 45, 46, that are connected to the ADC 38, as shown by the dotted lines.

This allows the current supplied across the subject to be accurately determined. In particular, by using the actual applied current as opposed to estimating the current applied on the basis of the control signals $I^+, I^-$, this takes into account non-ideal behaviour of the components in the current source, and can also take into account the effects of the leads 41, 42, on the applied current.

In one example, the amplifier $A_3$ and associated components may be provided on a housing coupled to the electrodes 12, 13, allowing more accurate sensing of the current applied to the subject. In particular, this avoids measuring of cable effects, such as signal loss in the leads L.

The above is an example of a non-symmetric current source and it will be appreciated that symmetric current sources may alternatively be used.

Figure 5:
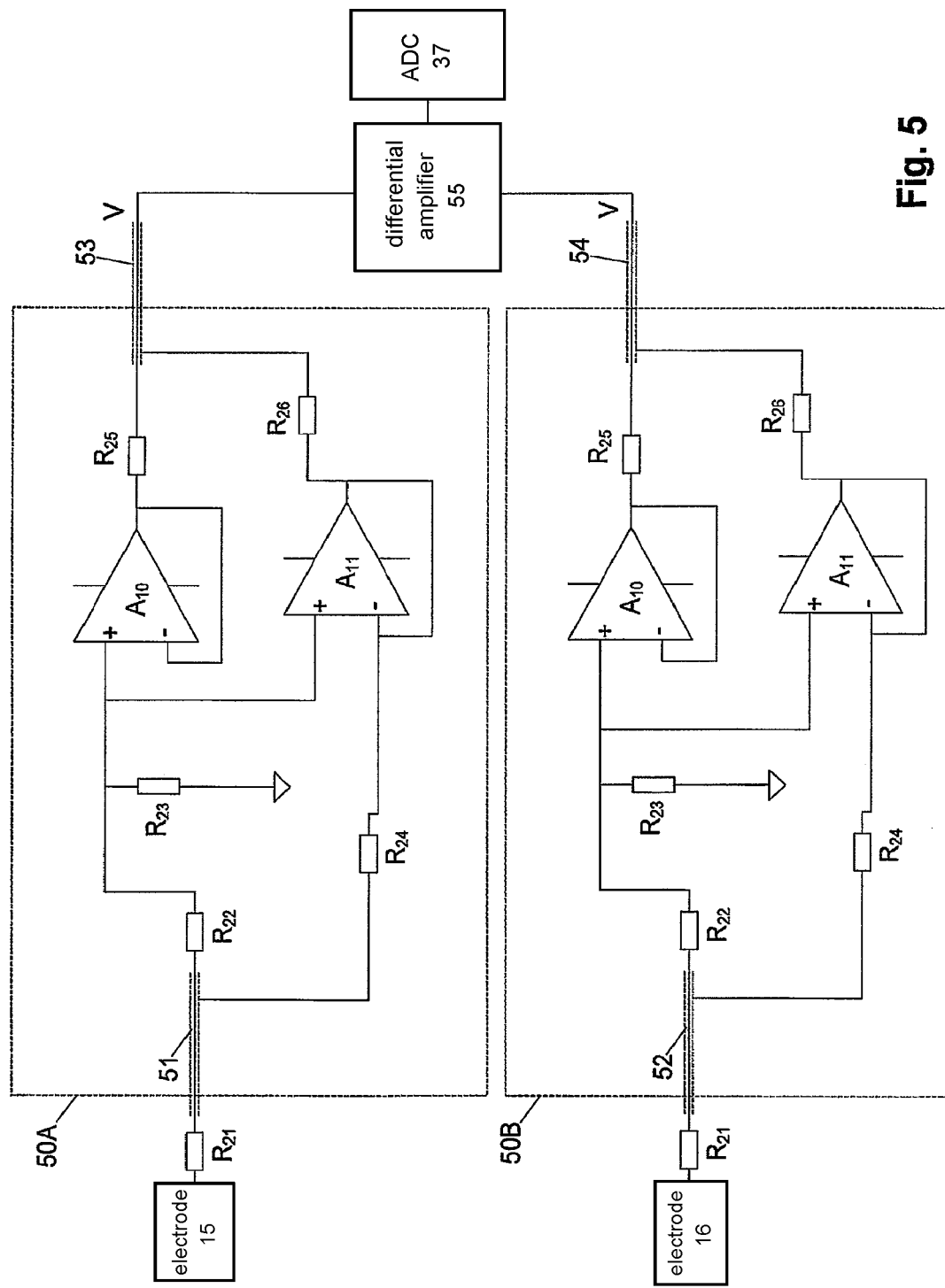
FIG. 5 is a schematic of an example of a buffer circuit for use in voltage sensing.

An example of the buffer used for the voltage electrodes is shown in FIG. 5. In this example, each electrode 15, 16, will be coupled to a buffer circuit 50A, 50B.

In this example, each buffer 50A, 50B includes amplifiers $A_{10}, A_{11}$, and a number of resistors $R_{21}, \ldots, R_{26}$, interconnected as shown. In use, each buffer 50A, 50B, is connected a respective electrode 15, 16 via connections 51, 52. The buffers 50A, 50B are also connected via leads 53, 54 to a differential amplifier 55, acting as the signal sensor 12, which is in turn coupled to the ADC 37. It will therefore be appreciated that a respective buffer circuit 50A, 50B is connected to each of the electrodes 15, 16, and then to a differential amplifier, allowing the potential difference across the subject to be determined.

In one example, the leads 53, 54 correspond to the leads L shown in FIG. 1, allowing the buffer circuits 50A, 50B to be provided in connector housing coupled to the electrodes 15, 16, as will be described in more detail below.

In use, the amplifier $A_{10}$ amplifies the detected signals and drives the core of the cable 53, whilst the amplifier $A_{11}$ amplifies the detected signal and drives the shield of the cables 51, 53. Resistors $R_{26}$ and $R_{25}$ decouple the amplifier outputs from the capacitances associated with cable, although the need for these depends on the amplifier selected.

Again, this allows multi-core shielded cables to be used to establish the connections to the voltage electrodes 15, 16.

Figure 6A:
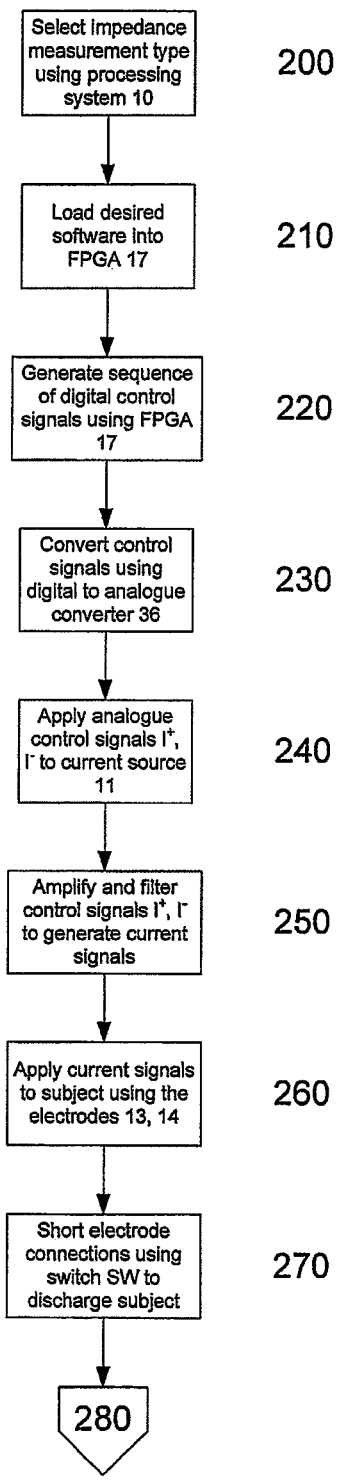
FIGS. 6A and 6B is a flowchart of a second example of a process for performing impedance determination.
Figure 6B:
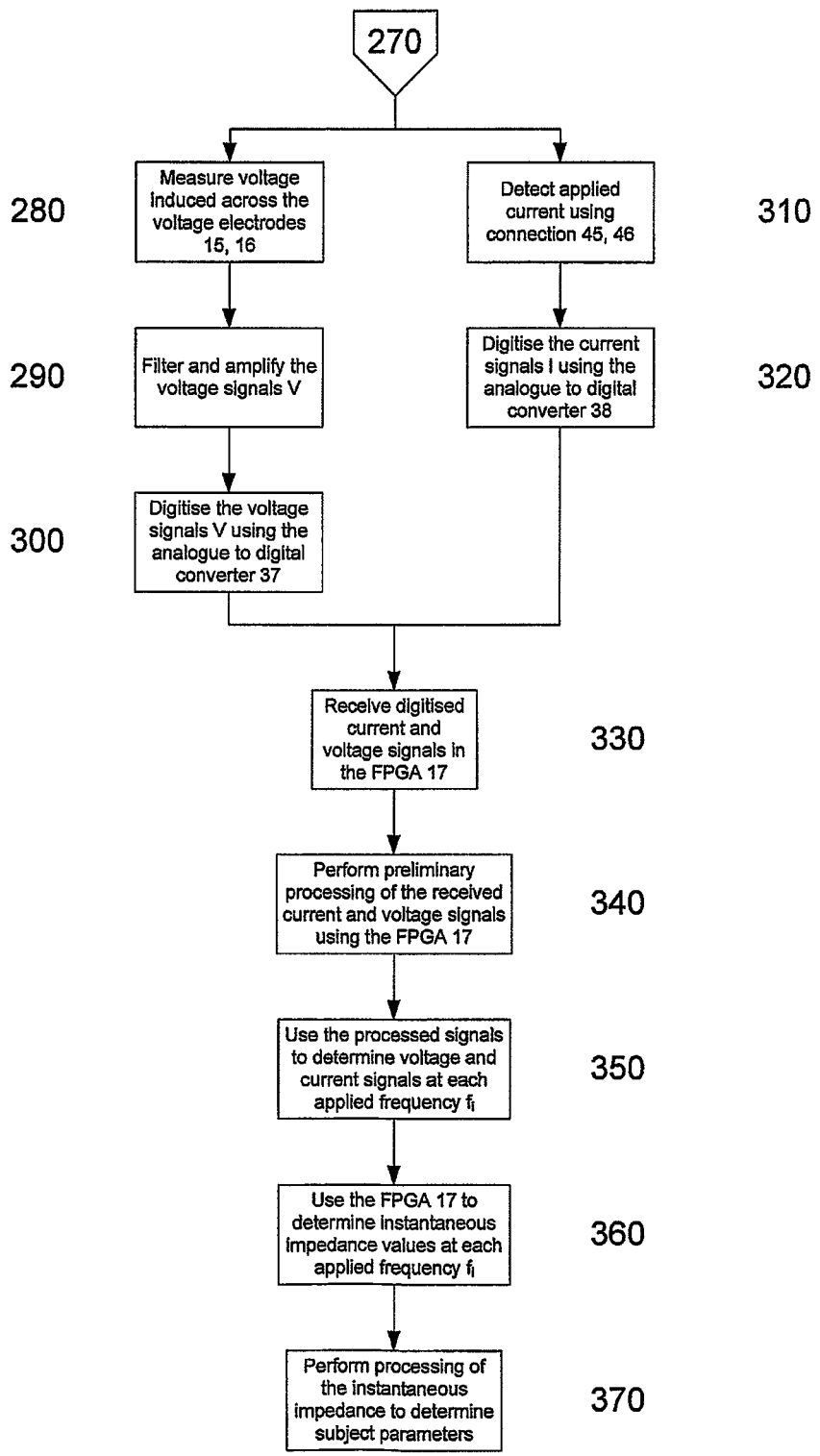

An example of operation of the apparatus will now be described with reference to FIGS. 6A to 6C.

At step 200 an operator selects an impedance measurement type using the first processing system 10. This may be achieved in a number of ways and will typically involve having the first processing system 10 stores a number of different profiles, each of which corresponds to a respective impedance measurement protocol.

Thus, for example, when using discrete electrode, it will be typical to use a different applied current sequence and a different impedance analysis, as compared to using band electrodes. The profile will typically be stored in the memory 21, or alternatively may be downloaded from flash memory (not shown), or via the external interface 23.

Once an appropriate measurement type has been selected by the operator, this will cause the first processing system 10 to load desired code module firmware into the programmable module 36 of the second processing system 17 at step 210, or cause embedded firmware to be activated. The type of code module used will depend on the preferred implementation, and in one example this is formed from a wishbone code module, although this is not essential.

At step 220, the second processing system 17 is used to generate a sequence of digital control signals, which are transferred to the DAC 39 at step 230. This is typically achieved using the processing module 34, by having the module generate a predetermined sequence of signals based on the selected impedance measurement profile. This can therefore be achieved by having the second processing system 17 program the processing module 34 to generate the required signals.

The DAC 39 converts the digital control signals into analogue control signals I+, I− which are then applied to the current source 11 at step 240.

As described above, the current source circuit shown in FIG. 4 operates to amplify and filter the electrical control signals I+, I− at step 250, applying the resulting current signals to the electrodes 13, 14 at step 260.

During this process, and as mentioned above, the current circuit through the subject can optionally be shorted at step 270, using the switch SW, to thereby discharge any residual field in the subject S, prior to readings being made.

At step 280, the measurement procedure commences, with the voltage across the subject being sensed from the electrodes 15, 16. In this regard, the voltage across the electrodes is filtered and amplified using the buffer circuit shown in FIG. 5 at step 290, with the resultant analogue voltage signals V being supplied to the ADC 37 and digitised at step 300. Simultaneously, at step 310 the current applied to the subject S is detected via one of the connections 45, 46, with the analogue current signals I being digitised using the ADC 38 at step 320.

The digitised voltage and current signals V, I are received by the processing modules 32, 33 at step 330, with these being used to performed preliminary processing of the signals at step 340.

The processing performed will again depend on the impedance measurement profile, and the consequent configuration of the processing modules 32, 33. This can include for example, processing the voltage signals V to extract ECG signals, The signals will also typically be filtered to ensure that only signals at the applied frequencies $f_i$, are used in impedance determination. This helps reduce the effects of noise, as well as reducing the amount of processing required.

At step 350 the second processing system 17 uses the processing signals to determine voltage and current signals at each applied frequency $f_i$, with these being used at step 360 to determine instantaneous impedance values at each applied frequency $f_i$.

The ADCs 37, 38 and the processing modules 32, 33 are typically adapted to perform sampling and processing of the voltage and current signals V, I in parallel so that the voltage induced at the corresponding applied current are analysed simultaneously. This reduces processing requirements by avoiding the need to determine which voltage signals were measured at which applied frequency. This is achieved by having the processing modules 32, 33 sample the digitised signals received from the ADCs 37, 38, using a common clock signal generated by the processing module 36, which thereby ensures synchronisation of the signal sampling.

Once the instantaneous impedance values have been derived, these can undergo further processing in either the first processing system 10, or the second processing system 17, at step 370. The processing of the instantaneous impedance signals will be performed in a number of different manners depending on the type of analysis to be used and this in turn will depend on the selection made by the operator at step 200.

Accordingly, it will be appreciated by persons skilled in the art that a range of different current sequences can be applied to the subject by making an appropriate measurement type selection. Once this has been performed, the FPGA operates to generate a sequence of appropriate control signals I+, I−, which are applied to the subject S using the current supply circuit shown in FIG. 4. The voltage induced across the subject is then sensed using the buffer circuit shown in FIG. 5, allowing the impedance values to be determined and analysed by the second processing system 17.

Using the second processing system 17 allows the majority of processing to be performed using custom configured hardware. This has a number of benefits.

Firstly, the use of a second processing system 17 allows the custom hardware configuration to be adapted through the use of appropriate firmware. This in turn allows a single measuring device to be used to perform a range of different types of analysis.

Secondly, this vastly reduces the processing requirements on the first processing system 10. This in turn allows the first processing system 10 to be implemented using relatively straightforward hardware, whilst still allowing the measuring device to perform sufficient analysis to provide interpretation of the impedance. This can include for example generating a "Wessel" plot, using the impedance values to determine parameters relating to cardiac function, as well as determining the presence or absence of pulmonary.

Thirdly, this allows the measuring device 1 to be updated. Thus for example, if an improved analysis algorithm is created, or an improved current sequence determined for a specific impedance measurement type, the measuring device can be updated by downloading new firmware via flash memory (not shown) or the external interface 23.

It will be appreciated that in the above examples, the processing is performed partially by the second processing system 17, and partially by the first processing system 10. However, it is also possible for processing to be performed by a single element, such as an FPGA, or a more generalised processing system.

As the FPGA is a customisable processing system, it tends to be more efficient in operation than a more generic processing system. As a result, if an FPGA alone is used, it is generally possible to use a reduced overall amount of processing, allowing for a reduction in power consumption and size. However, the degree of flexibility, and in particular, the range of processing and analysis of the impedance which can be performed is limited.

Conversely, if only a generic processing system is used, the flexibility is enhanced at the expensive of a decrease in efficiency, and a consequent increase in size and power consumption.

Accordingly, the above described example strikes a balance, providing custom processing in the form of an FPGA to perform partial processing. This can allow for example, the impedance values to be determined. Subsequent analysis, which generally requires a greater degree of flexibility can then be implemented with the generic processing system.

A further disadvantage of utilising an FPGA alone is that it complicates the process of updating the processing, for example, if improved processing algorithms are implemented.

Figure 7:
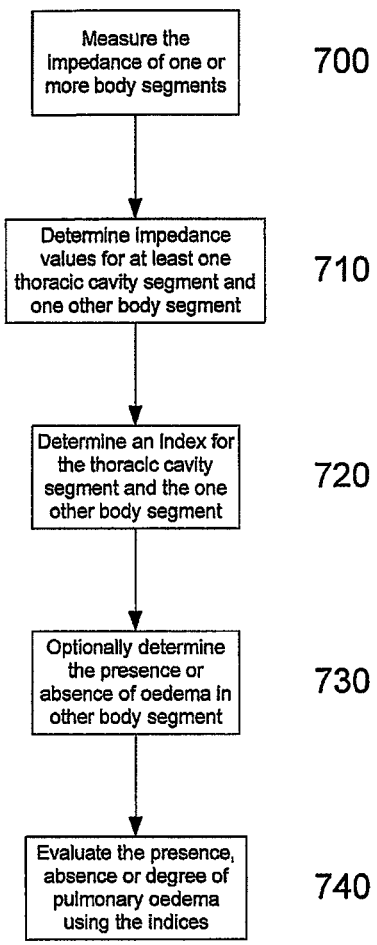
FIG. 7 is a flowchart of an example of a process for monitoring pulmonary oedema.

An example of the process for performing impedance measurements utilising the apparatus to FIG. 1 or FIG. 3 will now be described with reference to FIG. 7.

In particular, at step 700 the measuring device 1 is used to measure the impedance of one or more body segments. At step 710, the processing system 10 uses the measured impedances to determine impedance values for at least one thoracic cavity segment and one other body segment, with these being used in turn to determine an index for the thoracic cavity and the other body segments at step 720.

At step 730, the processing system 20, and/or the operator of the measuring device 1, optionally determines the presence, absence or degree of oedema in the other body segment. Following this, at step 740 the indices are used to determine the presence, absence, or degree of pulmonary oedema. This may be achieved in a number of manners depending on the implementation as will be described in more detail below.

Figure 8A:
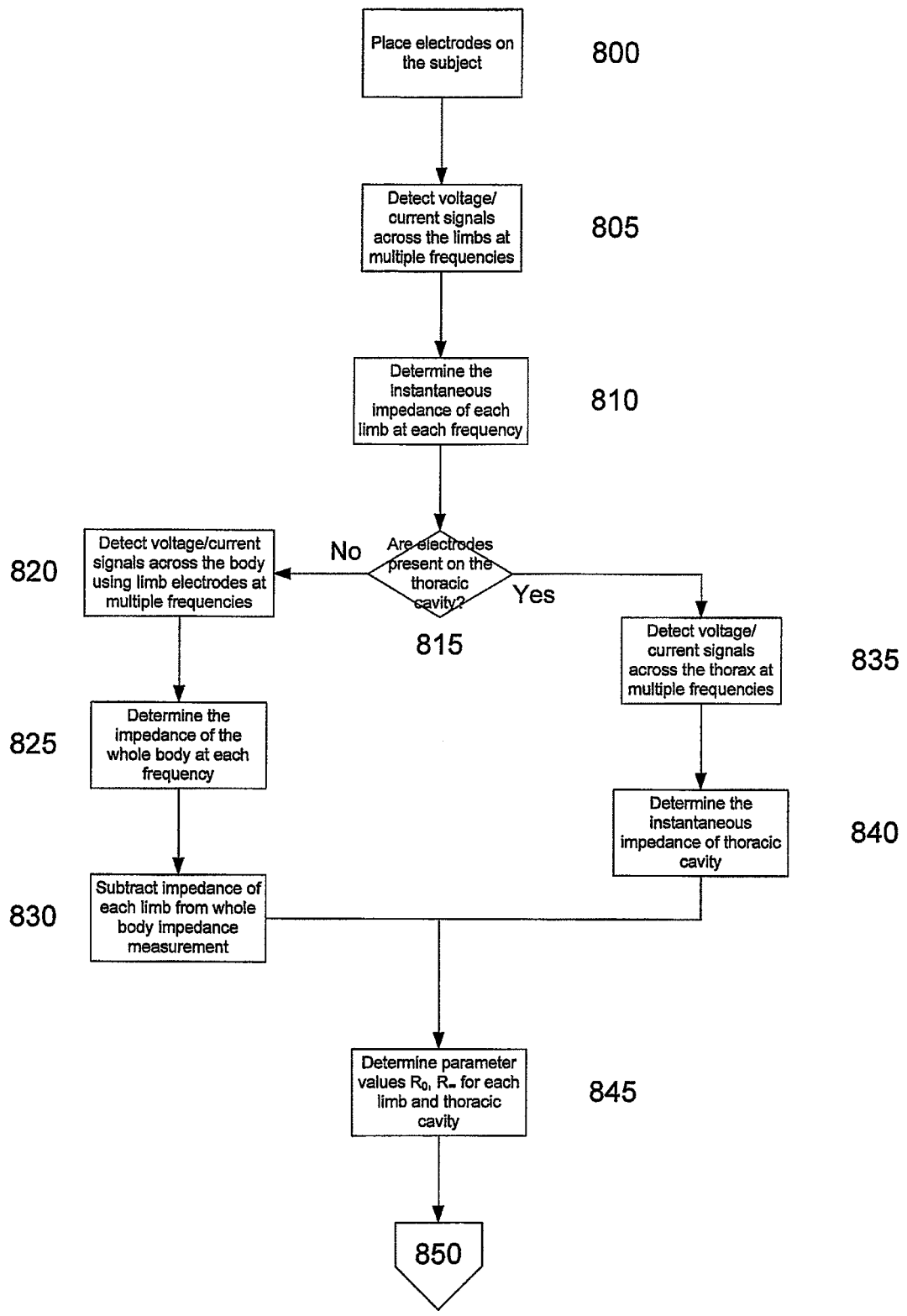
FIGS. 8A and 8B are a flow chart of a first specific example of a process for monitoring pulmonary oedema.
Figure 8B:
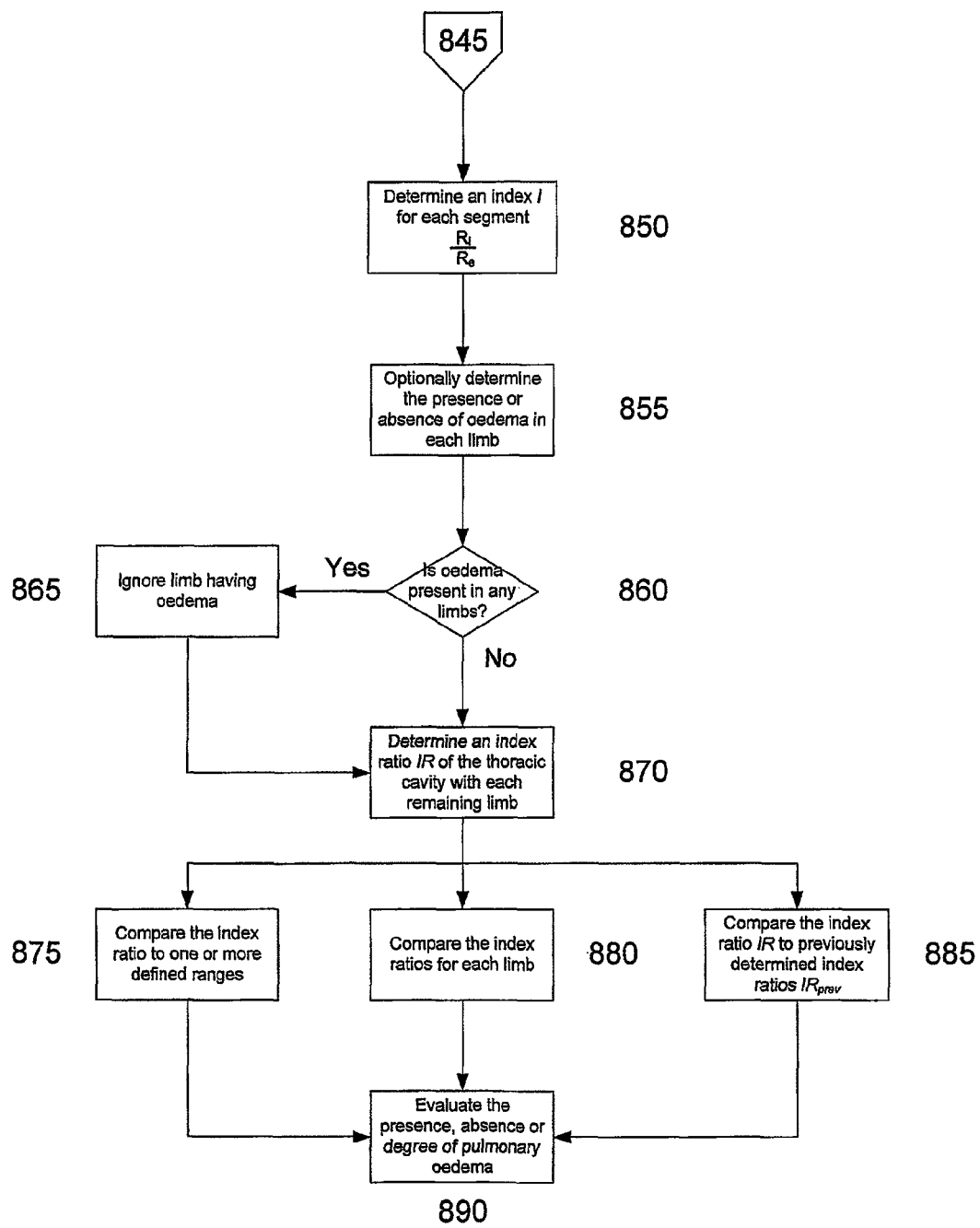

The exact manner in which the process is performed depends on the electrode configuration used, and hence the body segments for which impedance values are determined. A more detailed example will now be described with reference to FIGS. 8A and 8B, which sets out the process used for the electrode configurations of FIGS. 9A to 9E.

Figure 9A:
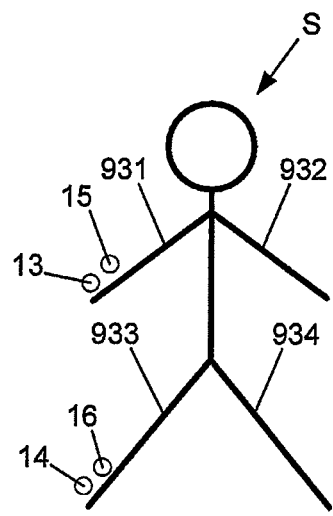
FIGS. 9A to 9E are schematic examples of electrode arrangements for use in the process of FIGS. 8A and 8B.
Figure 9B:
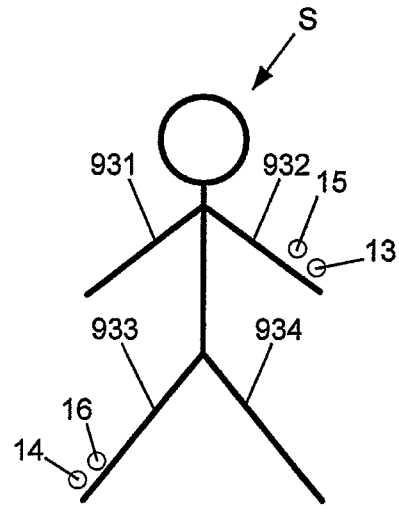

In this regard, the electrode configurations shown in FIGS. 9A to 9D involve positioning electrodes on the limbs of the subject S, with the particular electrode placement allowing the impedance of different body segments to be measured. Thus, for example, the impedance of a number of limbs can be measured. This can be achieved either in sequence, using a single channel system, or simultaneously, using a multi-channel system, as will be described in more detail below. In the examples of FIGS. 9A and 9B, the configuration allows the impedance of the entire subject to be determined, whereas the configurations shown in FIGS. 9C and 9D allow the right arm 931 and the right leg 933 to be measured respectively.

In general, when such an electrode arrangement is used, it is typical to provide electrodes in each possible electrode placement position, with leads being connected selectively to the electrodes as required. This will be described in more detail below.

It will be appreciated that this configuration uses the theory of equal potentials, allowing the electrode positions to provide reproducible results for impedance measurements. For example when current is injected between electrodes 13 and 14 in FIG. 9C, the electrode 16 could be placed anywhere along the left arm 932, since the whole arm is at an equal potential.

This is advantageous as it greatly reduces the variations in measurements caused by poor placement of the electrodes by the operator. It also greatly reduces the number of electrodes required to perform segmental body measurements, as well as allowing the limited connections shown to be used to measure each of limbs separately.

Figure 9C:
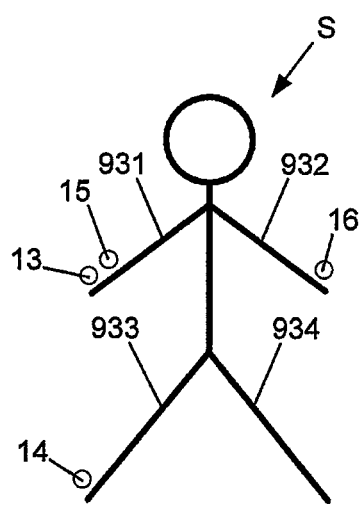
Figure 9D:
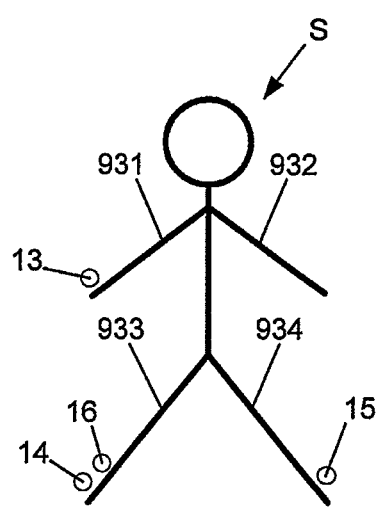
Figure 9E:
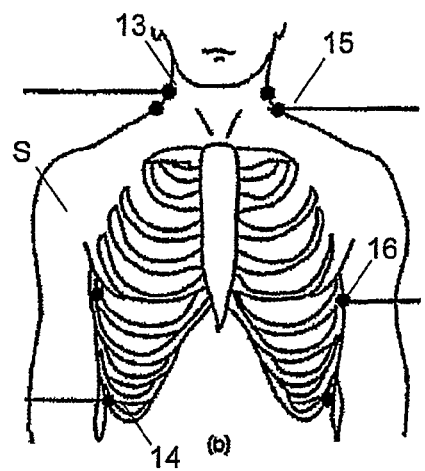

In FIG. 9E an alternative electrode configuration is shown in which the electrodes 13, 14, 15, 16 are band electrodes extending around the subject's neck and abdomen or spot electrodes as shown. This electrode configuration allows direct measurement of the impedance of the subjects thoracic cavity.

At step 800 electrodes 13, 14, 15, 16 are placed on the subject, with the measuring device 1 operating to apply appropriate current signals as described above, before detecting current and voltage signals across the limbs at multiple frequencies $f_i$, at step 805.

In order to achieve this, the electrode placements shown in FIGS. 9C and 9D are used, together with equivalent measurements being performed for contra-lateral limbs. The manner in which the electrode placement is coordinated will be described in more detail below.

The current signals used will depend on the preferred implementation and as described above could include applying current signals at multiple frequencies either simultaneously or in sequence, with appropriate processing of measured signals being performed to derive the measured voltage at each frequency.

At step 810 the processing system 10 operates to determine the instantaneous impedance of each limb at each of the frequencies $f_i$.

At step 815 the measuring device 1 operates to determine if electrodes are present on the thoracic cavity.

In the event that no such electrodes are provided at step 820, the measuring device 1 operates to detect voltage and current signals across the entire body using the one of the electrode configuration shown in FIGS. 9A and 9B.

At step 825 the processing system 10 operates to determine the impedance of the whole body at each frequency $f_i$. The measured impedance values obtained for each limb at each frequency $f_i$ are then subtracted from the impedance values measured at corresponding frequencies $f_i$ for the entire body at step 830. Subtracting the impedance measurements for each of the four limbs from the entire body impedance measurements provides an effective thoracic cavity impedance value at each frequency $f_i$.

In the event that electrodes are present on a thoracic cavity at step 835, the measuring device 1 operates to detect voltage and current signals across the thorax at multiple frequencies $f_i$, using this to determine instantaneous impedance values for the thoracic cavity at each frequency $f_i$ at step 840.

These values are then used to determine values for the impedance parameters $R_0$ and $R_\infty$ for each limb and the thoracic cavity, at step 845.

Figure 20:
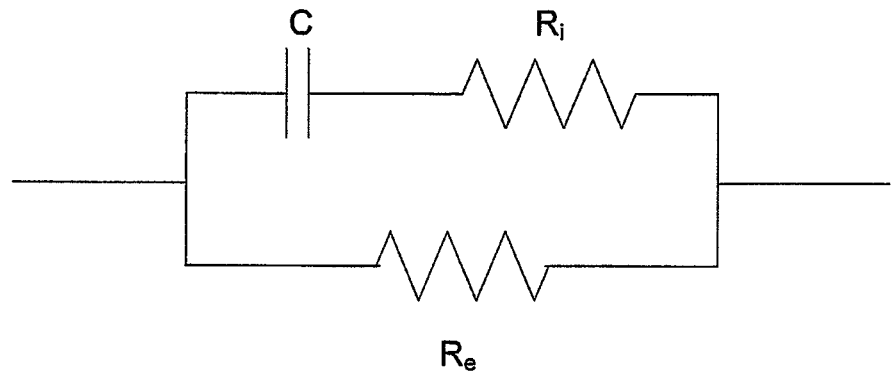
FIG. 20 is a schematic of an example of an equivalence circuit for modelling a subject's impedance response.

In this regard, FIG. 20 is an example of an equivalent circuit that effectively models the electrical behaviour of biological tissue. The equivalent circuit has two branches that represent current flow through extracellular fluid and intracellular fluid. The extracellular component of biological impedance is represented by $R_e$ and the intracellular component is represented by $R_i$. Capacitance of the cell membrane in the intracellular path is represented by C.

The relative magnitudes of the extracellular and intracellular components of impedance of an alternating current (AC) are frequency dependent. At zero frequency the capacitor acts as a perfect insulator and all current flows through the extracellular fluid, hence the resistance at zero frequency, $R_0$, equals $R_e$. At infinite frequency the capacitor acts as a perfect conductor and the current passes through the parallel resistive combination. The resistance at infinite frequency is given by $R_\infty = R_i R_e/(R_i+R_e)$.

Accordingly, the impedance of the equivalent circuit of FIG. 9 at an angular frequency $\omega$, where $\omega=2\pi*$frequency, is given by:

$$Z = R_\infty + \frac{R_0 - R_\infty}{1 + (j\omega\tau)} \quad (1)$$

where:
$R_\infty$=impedance at infinite applied frequency=$R_i R_e/(R_i+R_e)$,
$R_0$=impedance at zero applied frequency $R_e$ and,
$\tau$ is the time constant of the capacitive circuit.

However, the above represents an idealised situation which does not take into account the fact that the cell membrane is an imperfect capacitor. Taking this into account leads to a modified model in which:

$$Z = R_\infty + \frac{R_0 - R_\infty}{1 + (j\omega\tau)^{(1-\alpha)}} \quad (2)$$

where $\alpha$ has a value between 0 and 1 and can be thought of as an indicator of the deviation of a real system from the ideal model.

Figure 21:
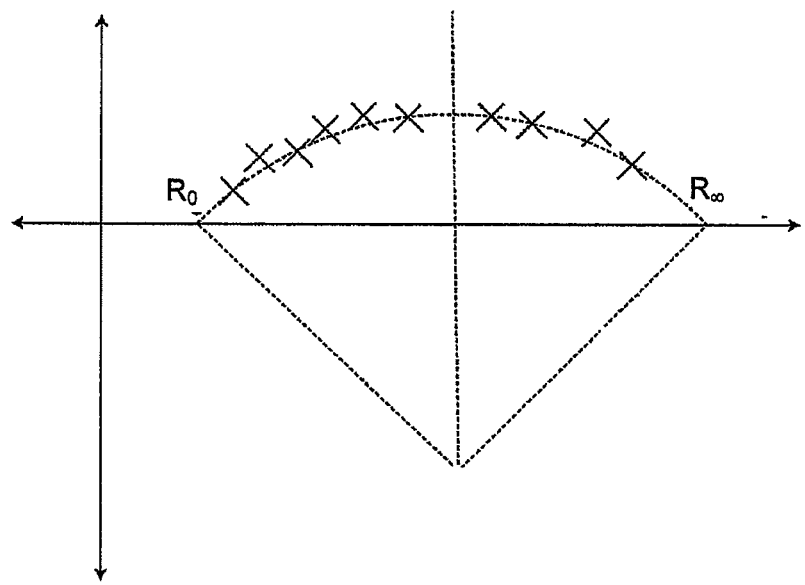
FIG. 21 is an example of a "Wessel" plot of a subject's admittance response.

The values of impedance parameters $R_0$ and $R_\infty$ may be determined in any one of a number of manners such as by:
  solving simultaneous equations based on the impedance values determined at different frequencies;
  using iterative mathematical techniques;
  extrapolation from a "Wessel plot" similar to that shown in FIG. 21;
  performing a function fitting technique, such as the use of a polynomial function.

The above described equivalent circuit models the resistivity as a constant value and does not therefore accurately reflect the impedance response of a subject, and in particular does not accurately model the change in orientation of the erythrocytes in the subject's blood stream, or other relaxation effects. To more successfully model the electrical conductivity of the human body, an improved CPE based model may alternatively be used.

In any event, it will be appreciated that any suitable technique for determination of the parameter values $R_0$ and $R_\infty$ may be used.

Once the parameter values $R_0$ and $R_\infty$ have been determined, the processing system 10 operates to determine an index I for each segment at step 850. In this example, the index used is given by $R_i/R_e$ and is indicative of the ratio of extracellular fluid to intracellular fluid.

In this regard, using the values for the extracellular fluid resistance $R_e$ and intracellular fluid resistance $R_i$ above, the index I is given by the equation:

$$I = \frac{R_i}{R_e} = \frac{R_\infty}{R_0 - R_\infty} \quad (3)$$

This approach has particular application to monitoring oedema over time as a plot of the index against time, or comparison of the index to other references, can disclose the onset and rate of advance of oedema.

This is possible, as, for a healthy subject; there is generally a degree of similarity of the extra- and intra-cellular fluid levels, even between different body segments. Thus, for example, if the subject is suffering from a condition other than oedema, which causes a general change in the ratio of extra- to intra-cellular fluid, then this should affect all body segments roughly equally.

At step 855 the measuring device 1 operates to optionally determine the presence or absence of oedema in each limb.

This may be performed in accordance with any one of a number of a techniques including, for example:
  comparing the index I for each of the limbs;
  medical examination; and,
  comparison of impedance parameter values and/or the index to previously monitor values known as a longitudinal analysis.

Thus, for example, the index I obtained for a limb can be compared to previously determined index values $I_{prev}$ obtained for the same limb, with variations in the index over time being indicative of the onset of oedema.

If it is determined that oedema is present in any of the limbs at step 860, the process moves on to step 865 with the processing system 10 operating to ignore the limb having oedema from subsequent analysis.

At step 870, for any limbs that do not have oedema, the processing system 10 operates to determine an index ratio IR based on a ratio of the index determined for the thoracic cavity with index determined for each remaining limb. Thus, for example, if it is determined that one leg, and both arms are free of oedema, three index ratios IR will be determined.

As mentioned above the index I should remain relatively constant for body regions that do not suffer from oedema, and accordingly, assuming that none of the body segments have oedema, then the index ratio IR should remain relatively constant for a given individual.

In particular, assuming that the properties of each body segment are equal, then the index ratio should have a value in the region of 1. Typically however, minor variations in tissue will occur between different body segments, and this can be accounted for in different ways.

Firstly, as shown at step 875, the index ratio IR can be compared to a predetermined range. In this case, the range is used to account for variations between impedance of the thoracic cavity and the limbs, which is not attributable to pulmonary oedema. It will therefore be appreciated that the range is therefore typically set to take into account the difference in index ratio IR between the thoracic cavity and the limbs in a number of different subjects. This range can therefore be set based on data collected from a number of healthy subjects.

In any event, if the index ratio IR falls outside the predetermined range, then this is used by the processing system 10 determine that pulmonary oedema is present in one of the body segments at step 890.

Furthermore, an assessment of the value of the index ratio IR can be used in assessing the degree of pulmonary oedema. Thus, for example, a number of value ranges can be defined, with each range corresponding to a different degree of oedema. In this instance, the processing system 10 can determine within which range the index ratio IR falls, and uses this to generate an indication of the likely degree of pulmonary oedema.

The value of the index ratio IR will also depend on the limbs that have been selected and accordingly, in general a different range will be selected for the comparison depending on the limbs under consideration.

The index ratio IR may also depend on a number of factors, such as the subject's age, weight, sex and height, and again a respective range can be selected based on these factors.

However, to avoid the need for an assessment of such factors, an alternative process of longitudinal analysis can be performed. In this case, at step 885, the processing system 10 can compare the index ratio IR to previously determined index ratios $IR_{prev}$ measured for the same subject, on the same body segments. In this situation, the previously determined index ratios $IR_{prev}$ are preferably determined prior to the onset of pulmonary oedema, although this is not essential.

In any event, previous measurements of the index ratio based on the same limbs on the same subject will automatically account for inherent variations in tissue properties, which in turn cause different values for the ratio of extra- to intra-cellular fluid even if pulmonary oedema is not present.

In this case, the processing system 10 assesses whether the current index ratio IR value is different to the previous index ratio $IR_{prev}$ determined for the same limb. If there is a change in the value, then the direction in change in value can indicate either increasing or decreasing levels of pulmonary oedema, with the magnitude of the change being used to indicate a degree of change at step 890.

A further option, as set out in step 880, is to compare the index ratios IR obtained for the different limbs. In this instance, each of the index ratios should be approximately equal as the index for each limb should be identical. In this instance, if there are variations between the index ratios IR which exceed a predetermined statistical significance, this can indicate either a problem with the measurement procedure, or the presence of tissue oedema in one of the limbs, which has been missed at step 860 above.

In general, at step 890, the processing system 10 will display an indication of one or more of:
one or more index ratios
one or more indexes; and,
the presence, absence or degree of pulmonary oedema.

It will therefore be appreciated from this that the above-described methodology provides different methods of determining the onset for oedema This can be achieved either by performing a longitudinal analysis in which the index ratio IR is compared to previously determined index ratios $IR_{prev}$. Alternatively the index ratio IR can be compared to one or more absolute index ratio ranges. Additionally, further checking can be provided by comparing the index ratios determined for the different limbs.

In practice, a combination of the approaches may be used. Thus, for example, when a patient is first admitted for a procedure to be performed, a comparison to absolute index ratio ranges may be used to confirm that it is unlikely that the patient has pulmonary oedema.

The measured index ratio IR can then be used to form the reference value of the index ratio $IR_{prev}$, allowing subsequent measurements to be compared thereto.

By using the index ratio IR described above, this allows variation in tissue properties between different body portions to be taken into account when assessing the presence, absence or degree of pulmonary oedema, and accordingly, this allows the onset of pulmonary oedema to be detected rapidly, accurately and at an early stage.

Figure 10:
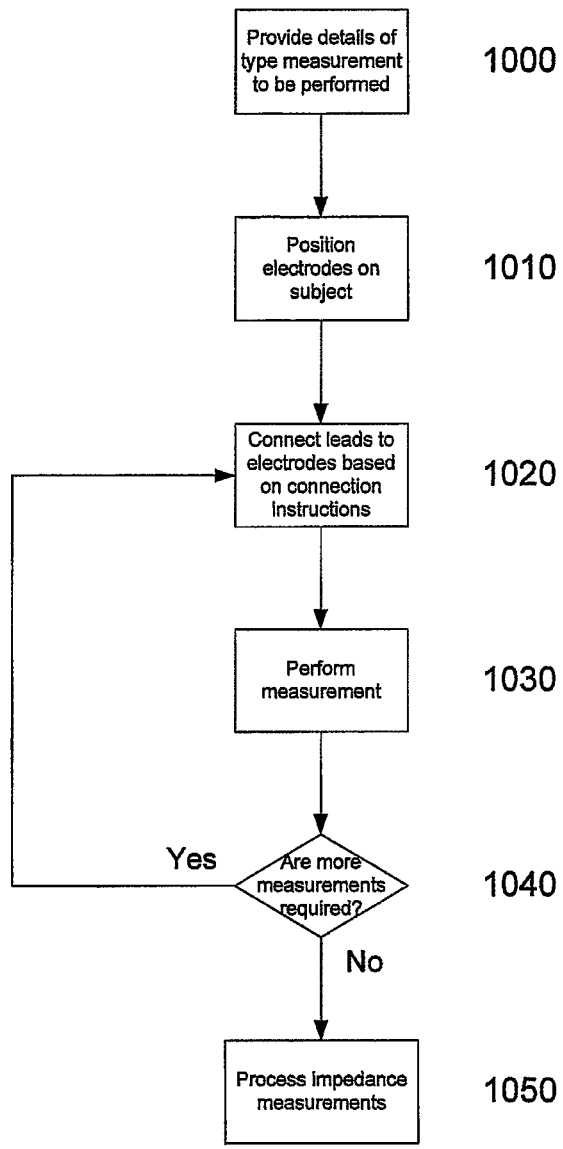
FIG. 10 is a flow chart of an example of a process for placing the electrodes in the process of FIGS. 8A and 8B.

An explanation of the process of electrode placement will now be described with reference to FIG. 10.

At step 1000 an operator of the apparatus provides details of a type of impedance measurement to be performed to the monitoring unit. Thus, for example, the operator will indicate that a pulmonary oedema assessment is to be performed, as well as indicating whether or not electrodes will be provided on the thorax as shown in FIG. 9E.

At step 1010 the operator positions electrodes on the subject, typically at each position where electrodes will be required during the measurement process. Following this the operator connects leads to the electrodes based on connection instructions provided by the monitoring unit at step 1020.

It will therefore be appreciated that this may be achieved in a number of ways and that typically, this involves having the measuring device 1 present a list of the available measurement types and allow the user to select the measurement type of interest. This can then be used to access a profile specifying the required electrode arrangement, which is then displayed to the user, allowing the user to correctly connect the electrodes.

At step 1030 the measuring device 1 will operate to perform impedance measurements by generating an appropriate current sequence and applying this to the subject via the electrodes 13, 14.

At step 1040 the measuring device 1 determines if further impedance measurements are required and if so the process returns to step 1010 to allow the operator to connect leads to different electrodes as required. This process is repeated until sufficient impedance measurements have been collected to perform the required analysis.

At this stage, the process moves on to step 1050 with the monitoring unit operating to process the impedance measurements and provide an indication of required information to the operator, as described above.

Figure 11A:
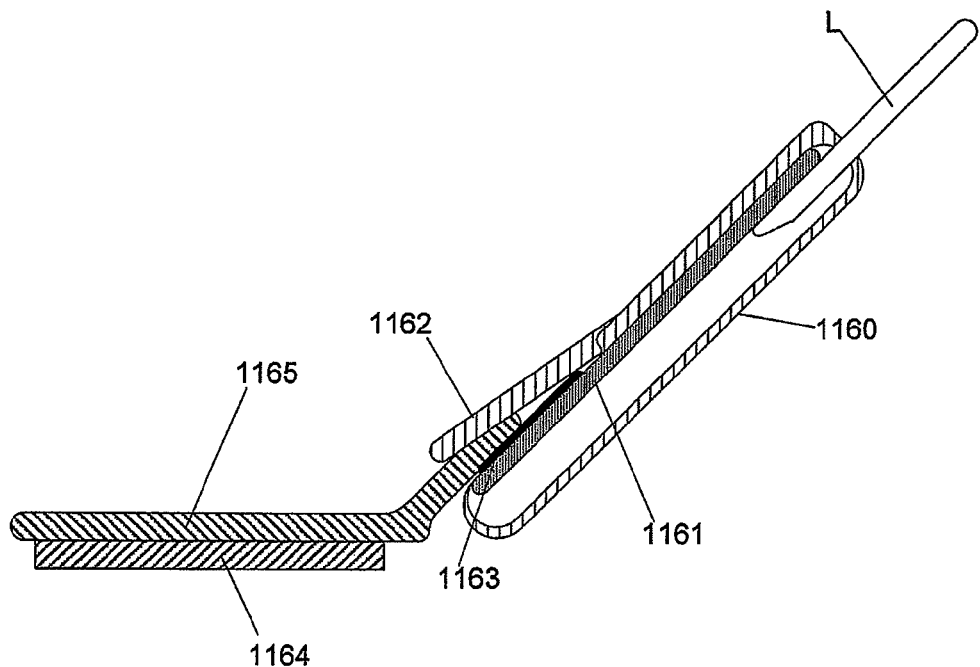
Figure 11B:
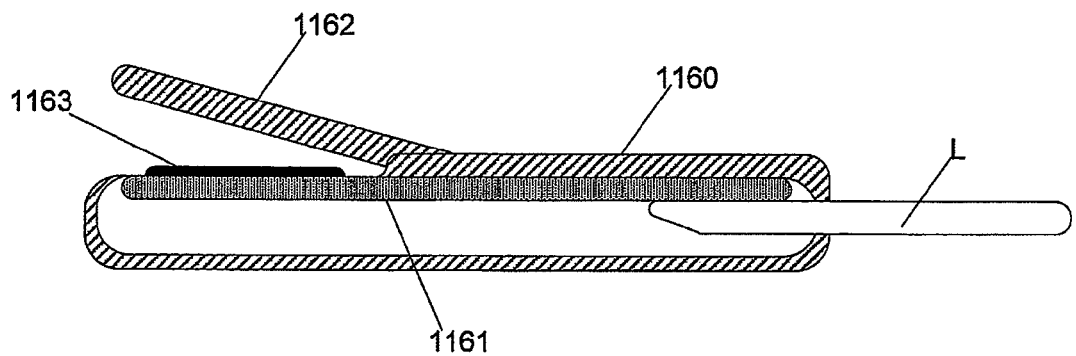

An example of an electrode connection apparatus that may be used in this process is shown in FIGS. 11A and 11B.

In particular, in this example, the connector includes circuitry provided on a substrate such as a PCB (Printed Circuit Board) 1161, which is in turn mounted in a housing 1160 as shown. The housing 1160 includes an arm 1162 which is urged toward a contact 1163 provided on the substrate 1161. The substrate 1161 is then coupled to a respective one of the ADCs 37, 38 or the DAC 39, via appropriate leads shown generally at L, such as the leads 41, 42, 53, 54.

In use, the connector couples to a conductive electrode substrate 1165, such as a plastic coated in silver, and which in turn has a conductive gel 1164, such as silver/silver chloride gel thereon. The arm 1162 urges the conductive electrode substrate 1165 against the contact 1163, thereby electrically coupling the conductive gel 1164 to the circuit provided on the substrate 1161.

This ensures good electrical contact between the measuring device 1 and the subject S, as well as reducing the need for leads between the electrodes 15, 16 and the input of the voltage buffers, removing the requirement for additional leads, which represents an expense, as well as a source of noise within the apparatus.

In this example, the edges and corners of the housing 1160, the arm 1162 and the substrate 1165 are curved. This is to reduce the chance of a subject being injured when the connector is attached to the electrode. This is of particular importance when using the electrodes on oedema suffers, when even a small nip of the skin can cause severe complications.

To further enhance the useability of the housing, the housing may be formed from a material that has a low coefficient of friction and/or is spongy or resilient. Again, these properties help reduce the likelihood of the subject being injured when the housing is coupled to the electrode.

Electrode Configuration

Figure 12A:
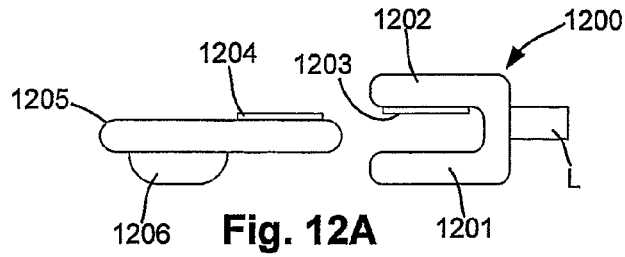
FIGS. 12A to 12G are schematic diagrams of a second example of an electrode connection.
Figure 12B:
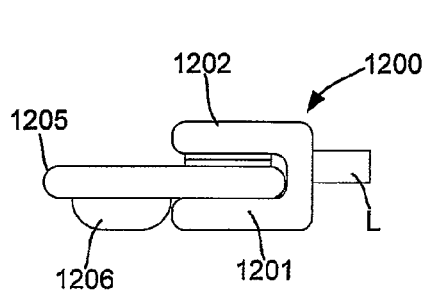
Figure 12C:
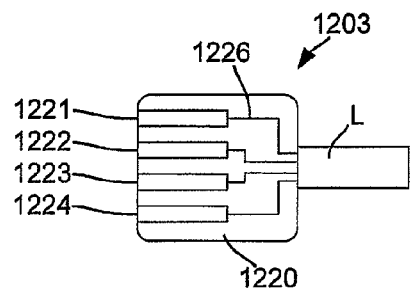
Figure 12D:
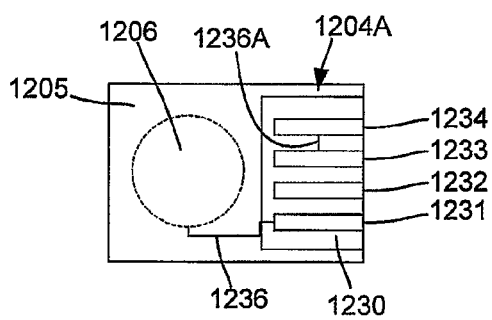
Figure 12E:
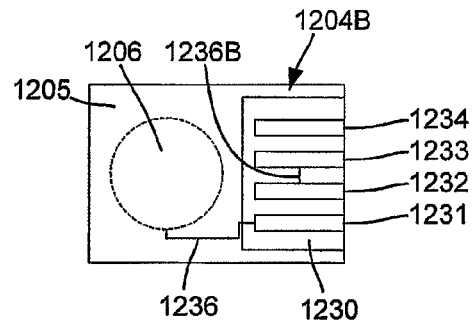
Figure 12F:
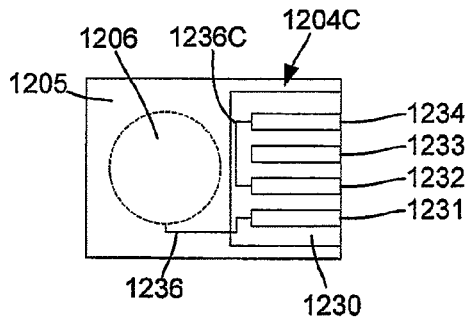
Figure 12G:
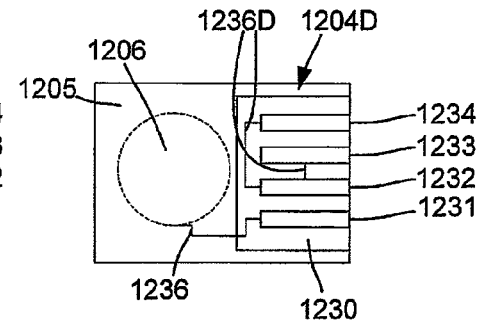

An example of an alternative electrode configuration will now be described with reference to FIGS. 12A and 12B.

In this example, the electrode connector is formed from a housing 1200 having two arms 1201, 1202 arranged to engage with an electrode substrate 1205 to thereby couple the housing 1200 to the substrate 1205. A contact 1203 mounted on an underside of the arm 1202, is urged into contact and/or engagement with an electrode contact 1204 mounted on a surface of the electrode substrate 1205. The electrode also includes a conductive gel 1206, such as a silver/silver chloride gel, electrically connected to the contact 1204. This can be achieved, either by using a conductive track, such as a silver track, or by using a conductive substrate such as plastic coated in silver.

This allows the lead L to be electrically connected to the conductive gel 1206, allowing current to be applied to and/or a voltage measured from the subject S to which they are attached. It will be appreciated that the above housing 1200 may contain the buffer circuit 50 or part of the current source circuit, in a manner similar to that described above.

Alternatively more complex interconnections may be provided to allow the measuring device 1 to identify specific electrodes, or electrode types.

This can be used by the measuring device 1 to control the measurement procedure. For example, detection of an electrode type by the processing system 2 may be used to control the measurements and calculation of different impedance parameters, for example to determine indicators for use in detecting oedema, monitoring cardiac function, or the like.

Similarly, electrodes can be provided with visual markings indicative of the position on the subject to which the electrode should be attached. For example a picture of a left hand can be shown if the electrode pad is to be attached to a subject's left hand. In this instance, identification of the electrodes can be used to allow the measuring device 1 to determine where on the subject the electrode is attached and hence control the application and measurement of signals accordingly.

An example of this will now be described with reference to FIGS. 12C to 12G. In this example the contact 1203 is formed from a contact substrate 1220, such as a PCB, having a number of connector elements 1221, 1222, 1223, 1224, formed from conductive contact pads, typically made of silver or the like. The connector elements are connected to the lead L via respective electrically conductive tracks 1226, typically formed from silver, and provided on the contact substrate 1220. The lead L includes a number of individual wires, each electrically coupled to a respective one of the connector elements 1221, 1222, 1223, 1224.

In this example the electrode contact 1204 on the electrode substrate 1205 typically includes an electrode contact substrate 1230, including electrode connector elements 1231, 1232, 1233, 1234, typically formed from silver contact pads or the like. The electrode connector elements 1231, . . . 1234 are positioned so that, in use, when the electrode connector 1200 is attached to an electrode, the connector elements 1221 . . . 1224 contact the electrode connector elements 1231, . . . 1234 to allow transfer of electrical signals with the measuring device 1.

In the examples, of FIGS. 12D to 12G, the connector element 1231 is connected to the conductive gel 1206, via an electrically conductive track 1236, typically a silver track that extends to the underside of the electrode substrate 1205. This can be used by the measuring device 1 to apply a current to, or measure a voltage across the subject S.

Additionally, selective ones of the connector elements 1232, 1233, 1234 are also interconnected in four different arrangements by respective connectors 1236A, 1236B, 1236C, 1236D. This allows the measuring device 1 to detect which of the electrode contacts 1222, 1223, 1224 are interconnected, by virtue of the connectors, 1236A, 1236B, 1236C, 1236D, with the four different combinations allowing the four different electrodes to be identified.

Accordingly, the arrangement of FIGS. 12D to 12G can be used to provide four different electrodes, used as for example, two current supply 13, 14 and two voltage measuring electrodes 15, 16.

In use, the measuring device 1 operates by having the second processing system 17 cause signals to be applied to appropriate wires within each of the leads L, allowing the conductivity between the connecting elements 1222, 1223, 1224, to be measured. This information is then used by the second processing system 17 to determine which leads L are connected to which of the electrodes 13, 14, 15, 16.

Figure 13:
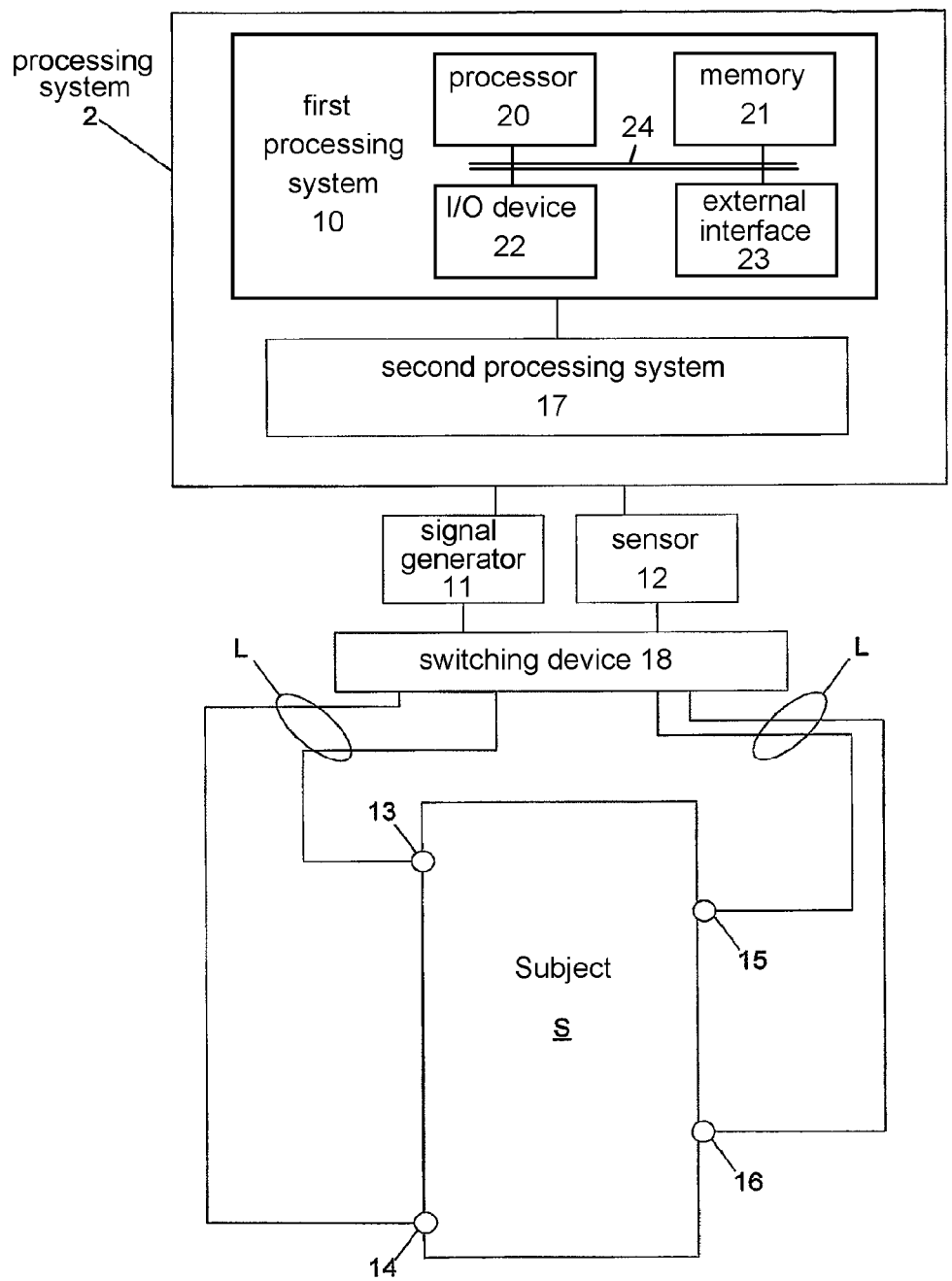
FIG. 13 is a schematic of a third example of impedance determination apparatus.

This allows the first processing system 10 or the second processing system 17 to control a multiplexer to connect the electrodes 13, 14, 15, 16 to the signal generator 12, or the signal sensor 12, as will now be described with respect to FIG. 13.

In this example, the measuring device 1 includes a switching device 18, such as a multiplexer, for connecting the signal generator 11 and the sensor 12 to the leads L. This allows the measuring device 1 to control which of the leads L are connected to the signal generator 11 and the sensor 12.

In this example, the individual applying the electrode pads to the subject can simply position the electrodes 13, 14, 15, 16 on the subject in the position indicated by visual markings provided thereon. Leads may then be connected to each of the electrodes allowing the measuring device 1 to automatically determine to which electrode 13, 14, 15, 16 each lead L connected and then apply current signals and measure voltage signals appropriately. This avoids the complexity of ensuring the correct electrode pads are connected via the correct leads L.

It will be appreciated that the above described process allows electrode identification simply by applying currents to the electrode connector. However, other suitable identification techniques can be used, such as through the use of optical encoding. This could be achieved for example, by providing a visual marker, or a number of suitably arranged physical markers on the electrode connector 1104, or electrode substrate 1105. These could then be detected using an optical sensor mounted on the connector 1100, as will be appreciated by persons skilled in the art. Alternatively, electrodes may be identified by an encoded value represented by a component such as a resistor or capacitor having a predetermined value.

A second detailed example of a process for determining pulmonary oedema will now be described with reference to FIG. 13.

Figure 14A:
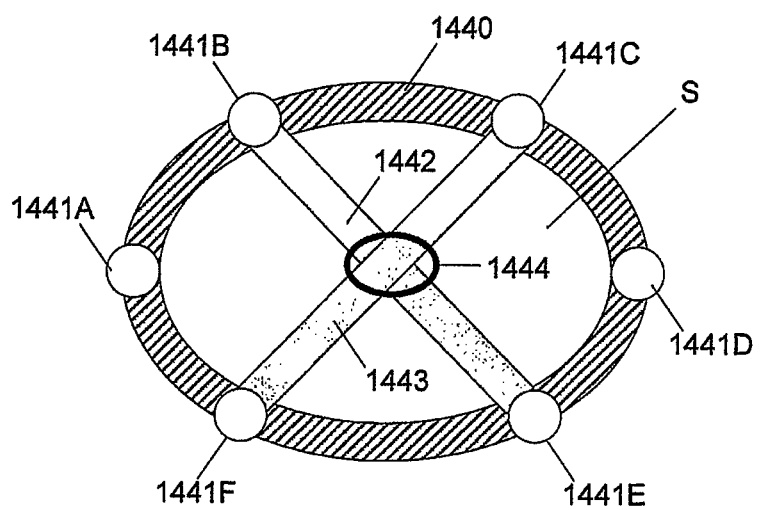
FIGS. 14A and 14B are schematic examples of electrode arrangements for use in the process of FIG. 15; and,
FIG. 15 is a flow chart of a second specific example of a process for monitoring pulmonary oedema.
Figure 14B:
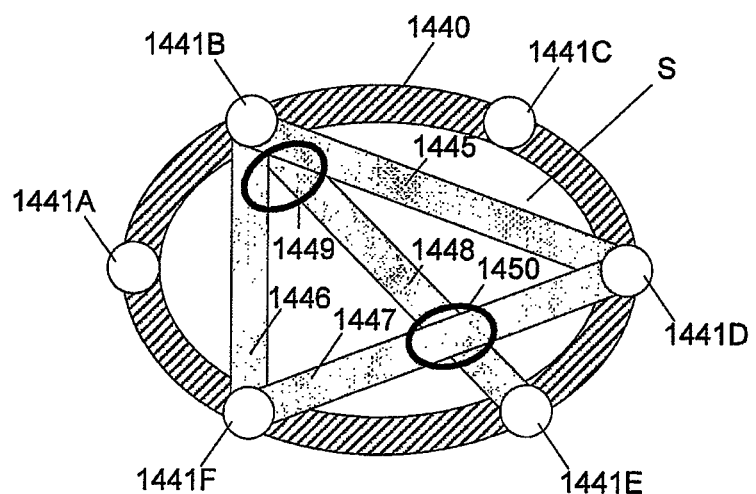
Figure 15:
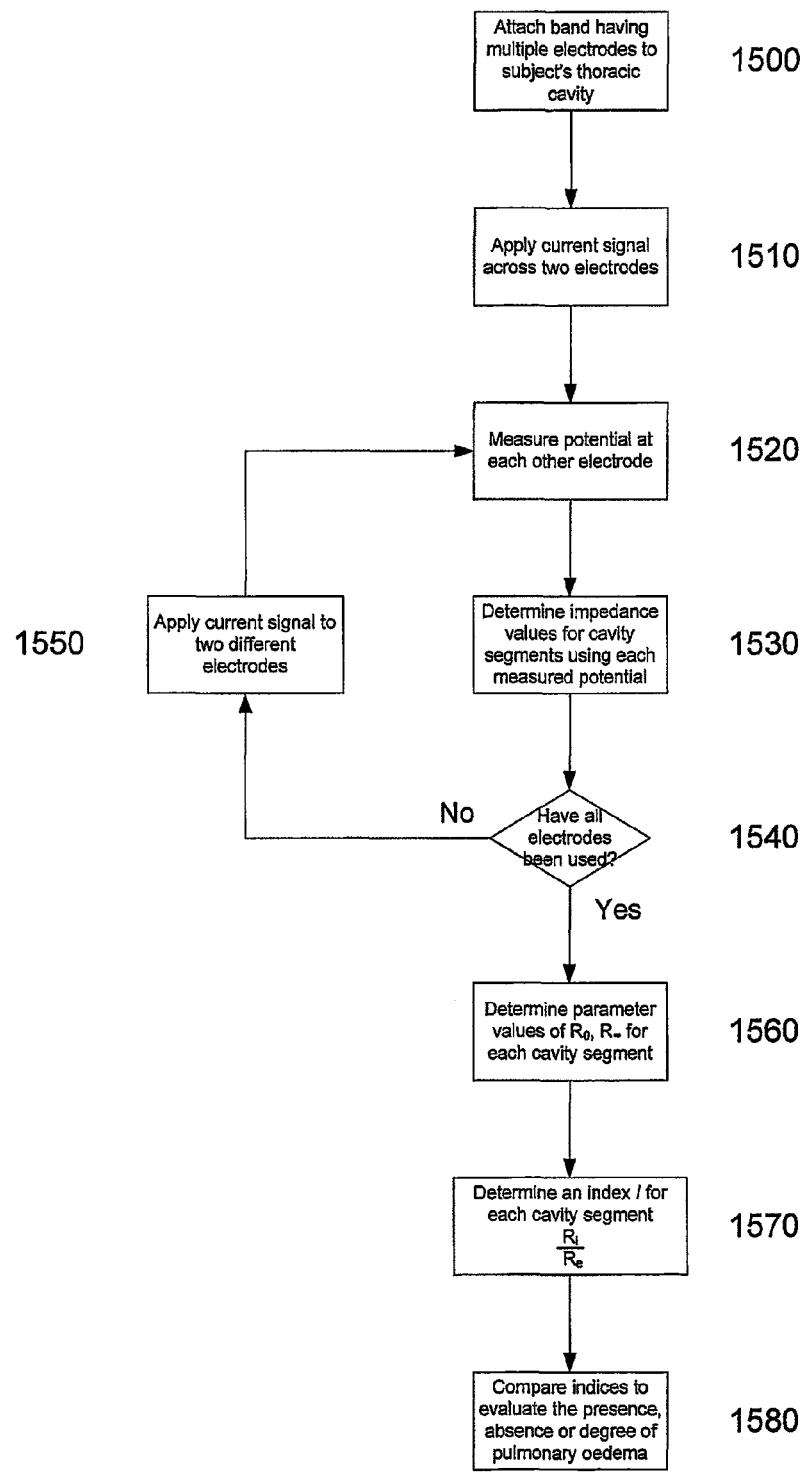

In particular, in this example, the process is performed using the electrode band shown in cross section in FIGS. 14A and 14B. As shown, the band electrode is formed from a band 1440 having a number of electrodes 1441A, . . . 41F provided thereon. In use, the band 1440 is adapted to be worn by the subject around the level of the xiphoid process, thereby allowing impedance measurements to be made directly from the subject's thoracic cavity. In this regard, each of the electrodes may be used as current or voltage electrodes as will be described.

In this example, at step 1500 the band 1440 is attached to the subject's thoracic cavity, with the measuring device 1 operating to apply a current signal across two of the electrodes at step 1510. In the example of FIG. 7A, the current supply is applied to the electrodes 1441A, 1441D so that the electrodes 1441A, 1441D act as the current supply electrodes 13, 14.

At step 1520, the measuring device 1 operates to measure the potential generated at each of the other electrodes 1441C, 1441D, 1441E, 1441F. The potentials are measured with respect to a common reference potential thereby allowing the potential measured at each electrode to be compared.

In particular, given the electrode configuration shown in FIG. 7A, it is apparent that the potentials generated at the electrodes 1441B, 1441F and similarly at the electrodes 1441C, 1441E will be identical, assuming a symmetrical impedance response for the subjects thoracic cavity. However, this allows comparison of the potentials between the electrodes, 1441C, 1441F, and between the electrodes 1441B, 1441B, as indicated at 1443, 1442 respectively.

By comparing the results of these comparisons, this allows the potential in a thoracic cavity segment 1444 to be determined, which in turn allows the first or second processing systems 10, 17 to determine impedance values for the cavity segment 1444 at step 1530.

It will be appreciated that when alternative electrode configurations are used, as shown for example in FIG. 14B, this allows different potential comparisons to be performed, which in turn allows the impedance of different thoracic cavity segments to be performed. Thus, for example, in the configuration shown in FIG. 14B, the electrodes 1441A, 1441C are used as the current supply electrodes, with potentials being measured at the electrodes 1441B, 1441D, 1441E, 1441F. This allows potential differences between the electrodes 1441B, 1441D; 1441B, 1441F; 1441D, 1441F; 1441B, 1441E, to be determined, as shown at 1445; 1446; 1447; 1448, thereby allowing impedance values to be determined for the cavity segments 1449, 1450.

Accordingly, this technique can utilise each possible electrode configuration, in other words with each possible pair of the electrodes 1441A, . . . , 1441F being used for current supply, allowing the impedance of a number of different cavity segments to be measured. It is also envisaged that all EIT approaches used to calculate the conductivity or impedances of thoracic segments known to people skilled in the art are envisaged to be contained in the scope of this disclosure.

Accordingly, at step 1554 the measuring device 1 determines if all possible electrode arrangements have been used and if not causes current signals to be applied to different electrodes 1441, with corresponding measurements and comparisons being performed at step 1020 and 1030.

Once measurements have been performed for all possible electrode configurations, the processing system 10 operates to determine parameter values $R_0$, $R_\infty$ for each possible cavity segment at step 1560. These parameter values are then used to determine an index for each cavity segment at step 1570. Whilst any index may be used, this is typically an index based on the ratio of the extra- to intra-cellular fluid, which can therefore be determined in a manner similar to that described above with respect to step 800 above.

At step 1580 the indices are used to evaluate the absence, presence or degree of oedema.

This may be achieved in a number of manners depending on the preferred implementation.

Thus, for example, this could be achieved by comparing the determined index values I to previously determined index values $I_{prev}$, such as measurements made before the onset of pulmonary oedema, thereby providing a form of longitudinal analysis, or by comparing the index values to predetermined reference ranges. Thus this can be performed in a manner similar to that described above with respect to steps 875 and 880.

Alternatively, the indices can be compared to each other directly. In this instance, it will be appreciated that if one of the thoracic cavity segments has an index value that is significantly different to the index values obtained for other cavity segments, then this indicates not only the presence of pulmonary oedema, but also its location.

In the above described example, six electrodes 1441 only are showed for clarity. However, it will be appreciated that any number of electrodes may be used, with a greater number of electrodes allowing a greater number of thoracic cavity segments to be analysed. This in turn can be used to provide a greater resolution and consequently, an improved diagnostic ability.

Additionally, whilst the band electrode is shown to extend all the way around the subject, this is not essential. In particular, in some applications, it is not possible to raise the subject from a surface, such as a bed, to allow the electrode band to be attached to the patient. In this instance, the electrode band could be adapted to extend only partially around the subjects thoracic cavity, as will be described in more detail below.

In this instance, or when an entire electrode band is used, it is also possible to provide multiple electrode bands spaced along the length of the thoracic cavity, thereby further enhancing the resolution of the detection process.

A further issue with the use of such band electrodes is that there can be significant variation in the thoracic cavity configuration during the respiration cycle. Accordingly it is typical for the current signal to use superposed signals, so that the impedances for each of the frequencies $f_i$ can be measured substantially simultaneously, thereby ensuring that variations in cavity configuration do not have an impact on any given impedance measurement.

In this instance, a further enhancement is to repeatedly measure the impedance of a given segment during the respiration process, thereby allowing variations in the impedance throughout the respiration cycle to be monitored. This can in turn be used to further enhance the detection of pulmonary oedema.

In order to implement this process, it will be appreciated that the band electrode may include a number of potential lead connections, with leads being connected to the band electrode manually, for example using a technique similar to that described above with respect to FIG. 10.

Preferably however an automated system is used in which leads are connected to each of the electrodes 1441 allowing automatic current application and measurement at the appropriate electrodes.

Figure 16:
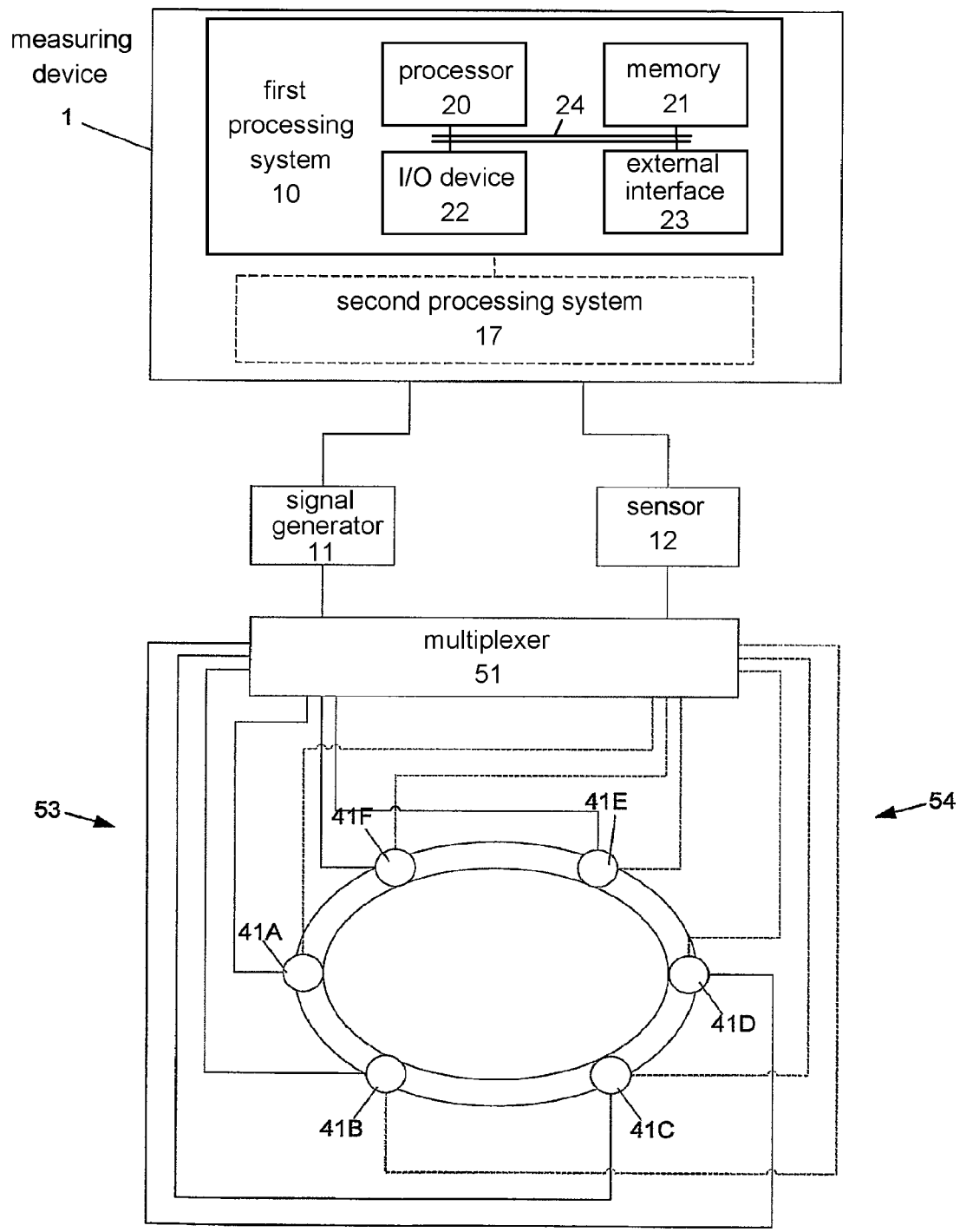
FIG. 16 is a schematic of a fourth example of apparatus for monitoring pulmonary oedema.

This may be achieved utilising apparatus shown in FIG. 16. In particular, this is similar to the apparatus shown in FIG. 1, but in this example includes a multiplexer 51 coupled to each of the electrodes by corresponding leads 53, 54 as shown.

In use, the multiplexing of signals can be controlled by the processing system 10, or the second processing system 17 if present, thereby allowing the measuring device 1 to apply a current to each possible electrode pair in turn, measuring the resulting potentials at each of the remaining electrodes automatically.

This has the added advantage of allowing a band electrode to be placed on the subjects abdomen with measurements being performed rapidly and automatically by the measuring device 1. This makes the apparatus and method suitable for home care applications in which individuals at risk of pulmonary oedema are provided with their own measuring device 1 and instructed how to take their own measurements. This can be achieved simply by wearing the band electrode and then activating the measuring device 1, it will be appreciated that this provides a simple mechanism for inexperienced individuals to take their own readings and be alerted in the event that pulmonary oedema is a risk.

Band Electrode Example

An example of an alternative electrode configuration will now be described with reference to FIGS. 17A to 17F. In this particular example the electrode is a band electrode 1700, which includes a number of separate electrodes. In this example the electrode is formed from an elongate substrate 1710 such as a plastic polymer coated with shielding material and an overlaying insulating material.

A number of electrically conductive tracks 1720 are provided on the substrate extending from an end of the substrate 1711 to respective conductive contact pads 1730, spaced apart along the length of the substrate in sequence. This allows a connector similar to the connectors described above, but with corresponding connections, to be electrically coupled to the tracks 1220.

The tracks 1720 and the contact pads 1730 may be provided on the substrate 1710 in any one of a number of manners, including for example, screen printing, inkjet printing, vapour deposition, or the like, and are typically formed from silver or another similar material. It will be appreciated however that the tracks and contact pads should be formed from similar materials to prevent signal drift.

Following the application of the contact pads 1730 and the tracks 1720, an insulating layer 1740 is provided having a number of apertures 1750 aligned with the electrodes contact pads 1730. The insulating layer is typically formed from a plastic polymer coated with shielding material and an overlaying insulating material.

To ensure adequate conduction between the contact pads 1730, and the subject S, it is typical to apply a conductive gel 1760 to the contact pads 1730. It will be appreciated that in this instance gel can be provided into each of the apertures 1750 as shown.

A removable covering 1770 is then applied to the electrode, to maintain the electrode's sterility and/or moisture level in the gel. This may be in the form of a peel off strip or the like which when removed exposes the conductive gel 1760, allowing the electrode to be attached to the subject S.

In order to ensure signal quality, it is typical for each of the tracks 1720 to comprise a shield track 1721, and a signal track 1722, as shown. This allows the shield on the leads L, such as the leads 41, 42, 51 to be connected to the shield track 1721, with the lead core being coupled to the signal track 1722. This allows shielding to be provided on the electrode, to help reduce interference between applied and measured signals.

This provides a fast straight-forward and cheap method of producing band electrodes. It will be appreciated that similar screen printing techniques may be utilised in the electrode arrangements shown in FIGS. 11A and 11B, and 12A-12G.

The band electrode may be utilised together with a magnetic connector as will now be described with respect to FIGS. 17G and 17H. In this example, the band electrode 1700 includes two magnets 1701A, 1701B positioned at the end 1711 of the substrate 1710. The connector is formed from a connector substrate 1780 having magnets 1781A, 1781B provided therein. Connecting elements 1782 are also provided, and these would in turn be connected to appropriate leads L.

The magnets 1701A, 1781A; 1701B (not shown for clarity), 1781B can be arranged to align and magnetically couple, to urge the connector substrate 1780 and the band electrode 1700 together. Correct alignment of the poles of the magnets 1701A, 1781A; 1701B, 1781B can also be used to ensure both the correct positioning and orientation of the connector substrate 1780 and band electrode, which can ensure correct alignment of the connecting elements 1781, with corresponding ones of the tracks 1720, on the band electrode 1700.

It will be appreciated that this can be used to ensure correct connection with the electrode, and that a similar magnetic alignment technique may be used in the connectors previously described.

Figure 17I:
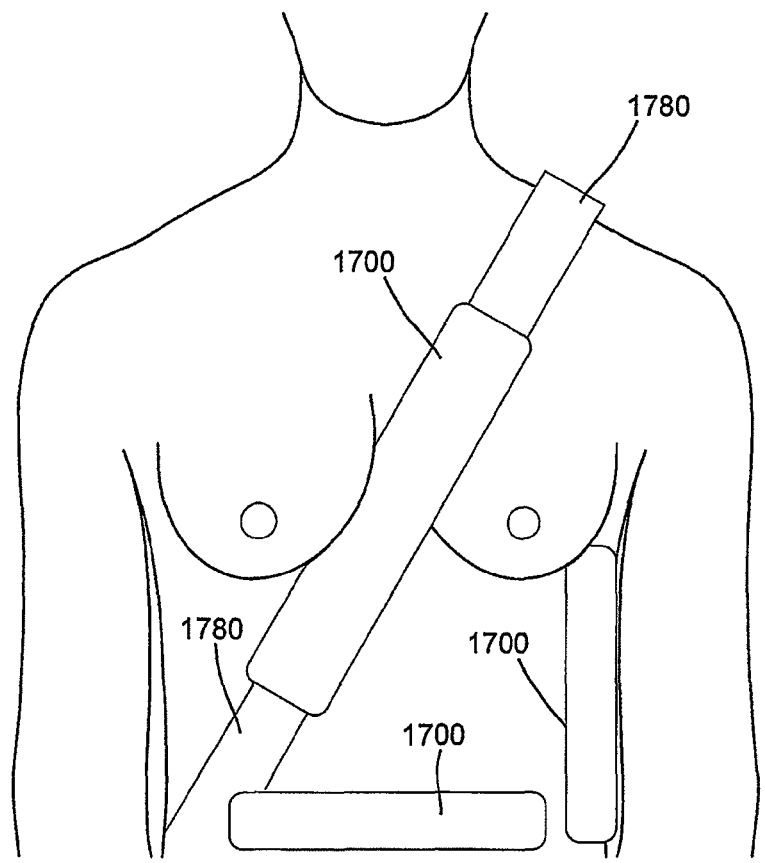
FIG. 17I is a schematic diagram of the use of a band electrode.
Figure 17A:
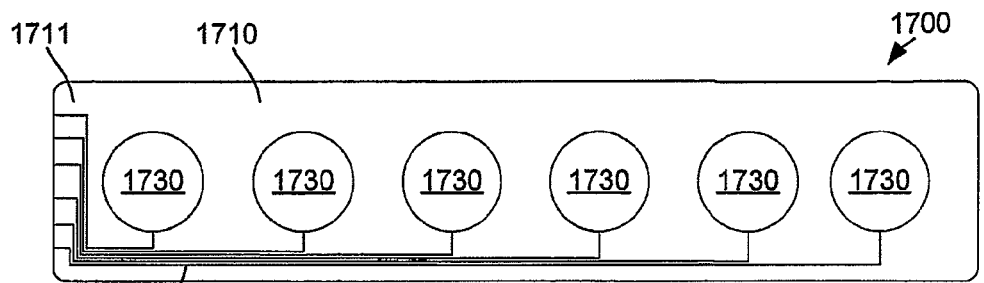
FIGS. 17A to 17F are schematic diagrams of an example of the construction of a band electrode.
Figure 17B:
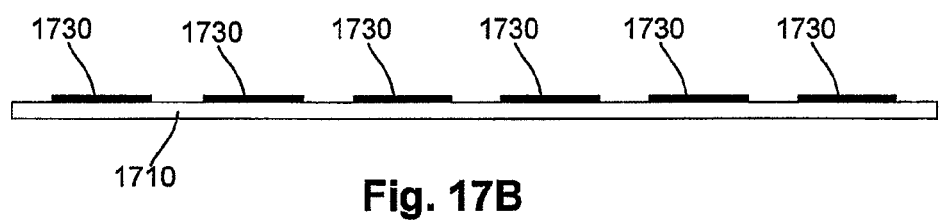
Figure 17C:
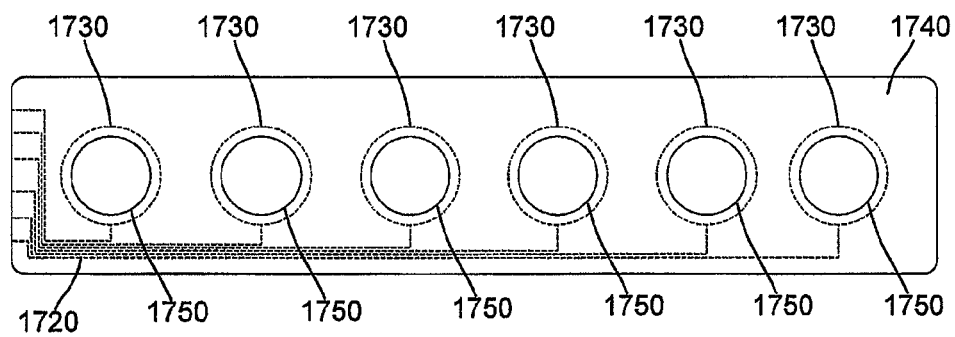
Figure 17D:
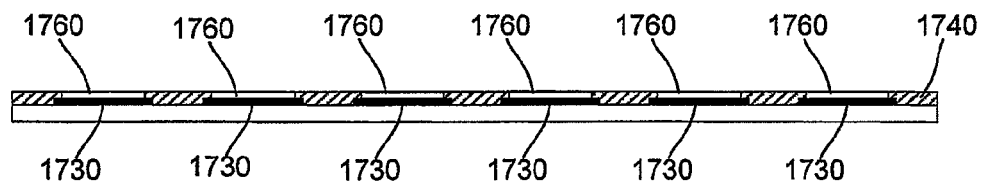
Figure 17E:
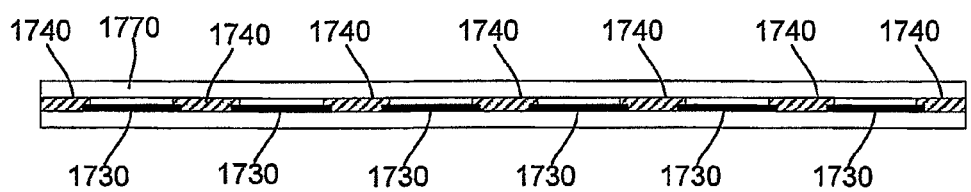
Figure 17F:
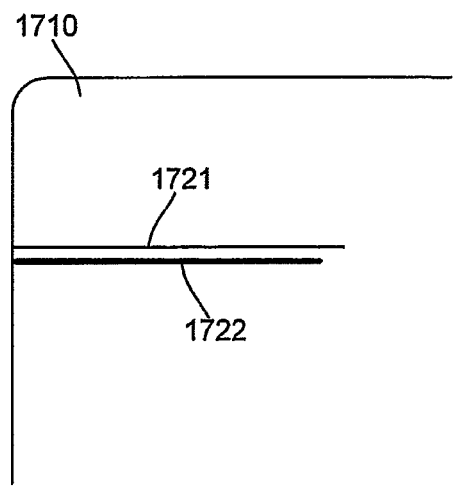
Figure 17G:
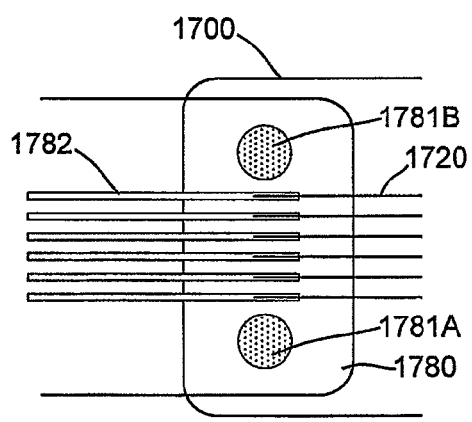
FIGS. 17G and 17H are schematic diagrams of an example of a connector arrangement for the band electrode.
Figure 17H:
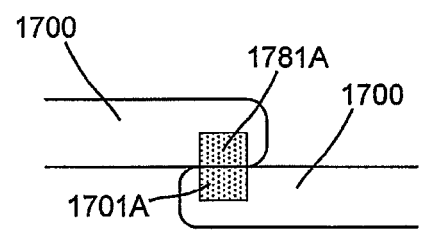

In use, the band electrode may be attached to the subject's torso, as shown in FIG. 17I. The electrode will typically include an adhesive surface, allowing it to stick to the subject. However, a strap 1780 may also be used, to help retain the electrode 1700 in position. This provides an electrode that is easy to attach and position on the subject, and yet can be worn for an extended period if necessary. The band electrode 1700 may also be positioned on the subject at other locations, such as on the side of the subject's torso, or laterally above the naval, as shown.

The band electrode 1700 provides sufficient electrodes to allow cardiac function to be monitored. In the above example, the band electrode includes six electrodes, however any suitable number may be used, although typically at least four electrodes are required.

Variable Current

A further feature that can be implemented in the above measuring device is the provision of a signal generator 11 capable of generating a variable strength signal, such as a variable current. This may be used to allow the measuring device 1 to be utilised with different animals, detect problems with electrical connections, or to overcome noise problems.

Figure 18:
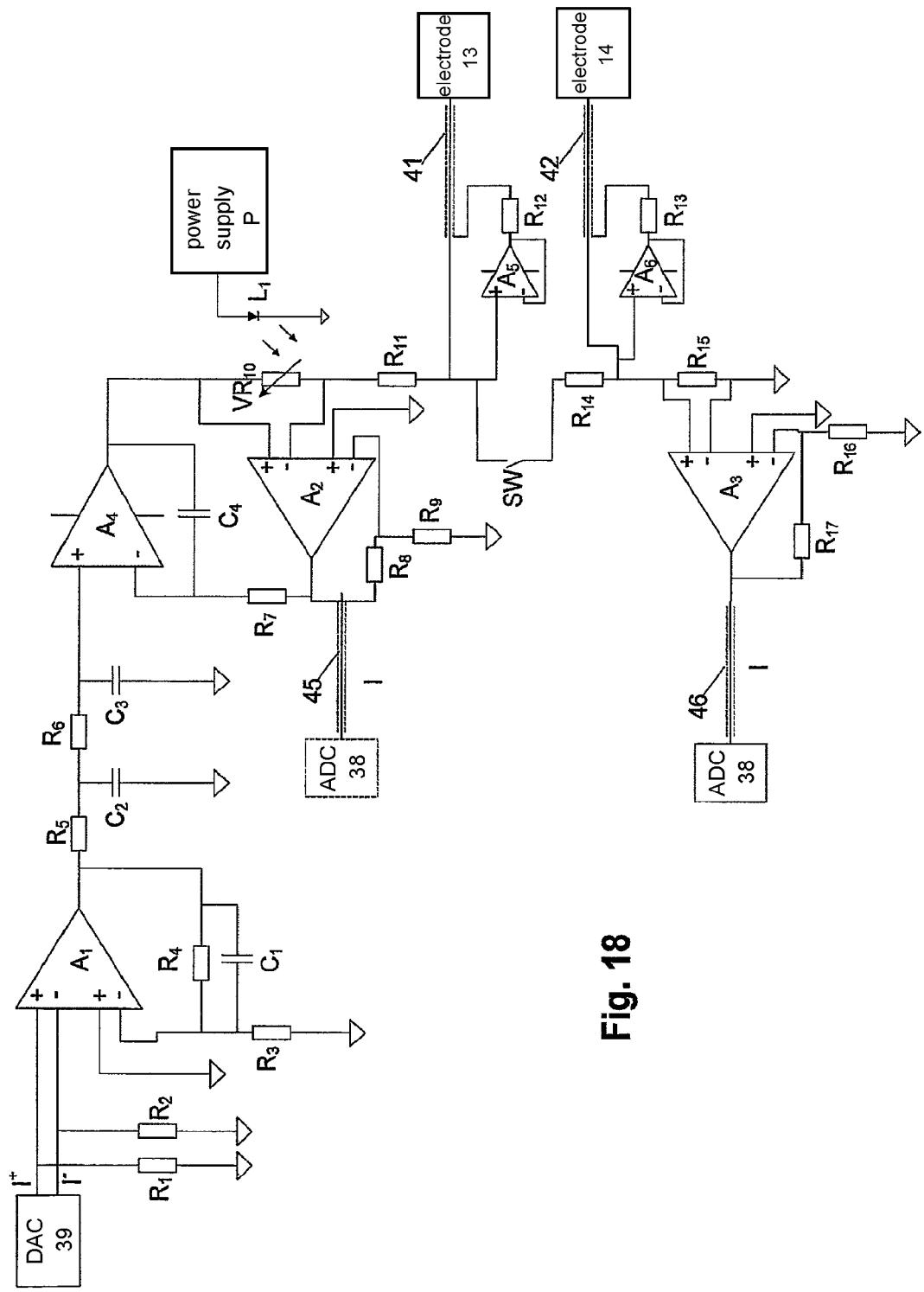
FIG. 18 is a schematic of a second example of a current source circuit.

In order to achieve this, the current source circuit shown in FIG. 4 is modified as shown in FIG. 18. In this example, the resistor $R_{10}$ in the current source circuit of FIG. 4 is replaced with a variable resistor $VR_{10}$. Alteration of the resistance of the resistor $VR_{10}$ will result in a corresponding change in the magnitude of the current applied to the subject S.

To reduce noise and interference between the current source circuit and the control, which is typically achieved using the second processing module 17, it is typical to electrically isolate the variable resistor 17 from the control system. Accordingly in one example, the variable resistor $VR_{10}$ is formed from a light dependent resistor. In this example, a light emitting diode (LED) or other illumination source can be provided, as shown at $L_1$. The LED $L_1$ can be coupled to a variable power supply P of any suitable form. In use, the power supply P, is controlled by the second processing module 17, thereby controlling the intensity of light generated by the LED $L_1$, which in turn allows the resistance $VR_{10}$, and hence the applied current, to be varied.

Figure 19:
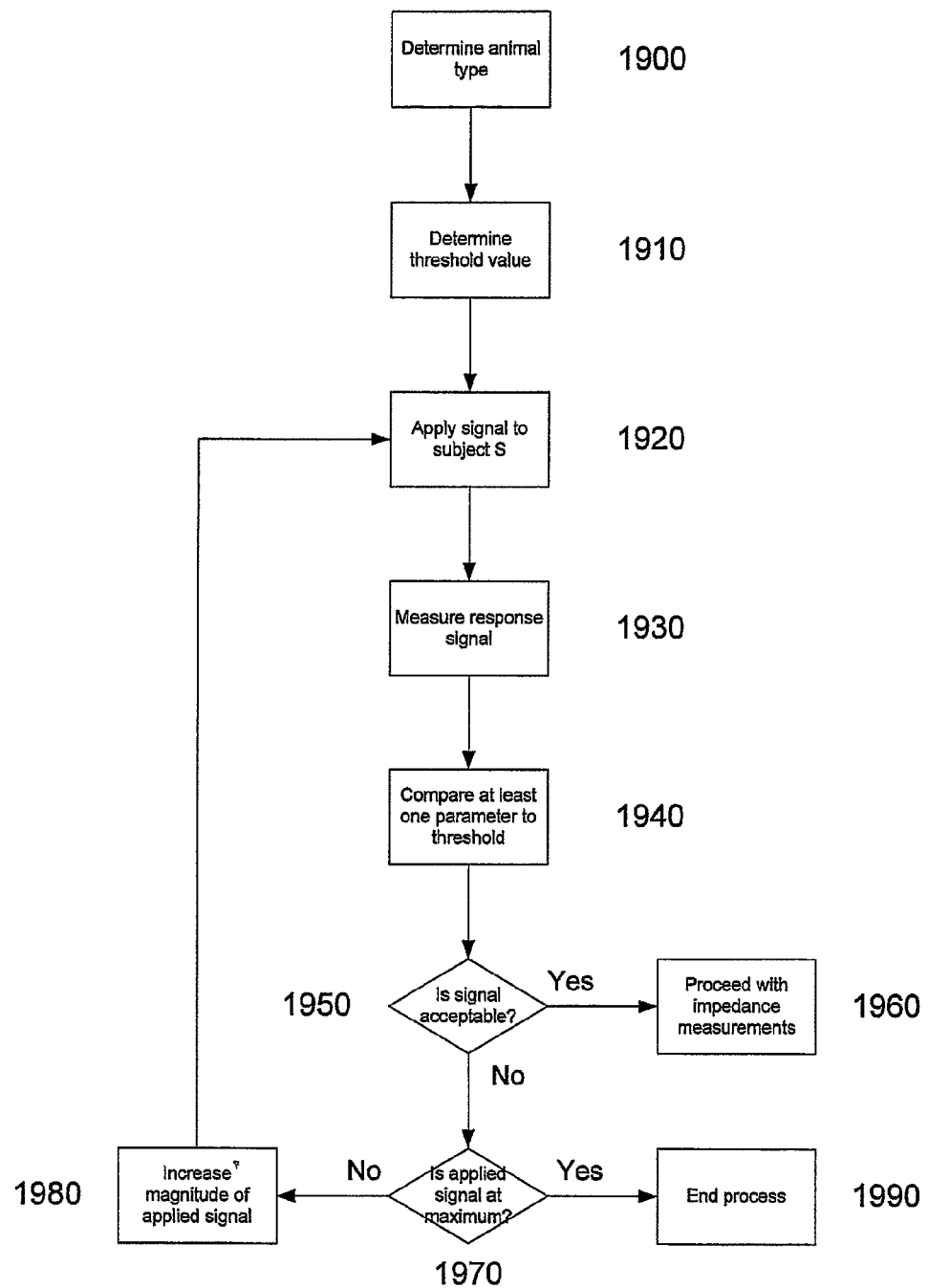
FIG. 19 is a flow chart of an example of using the current source circuit of FIG. 17.

In order to operate the measuring device 1, the first processing system 10 and the second processing system 17 typically implement the process described in FIG. 19. In this example, at step 1900 the user selects a measurement or an animal type utilising the input/output device 22.

At step 1910 the first processing system 10 and the second processing system 17 interact to determine one or more threshold values based on the selected measurement or animal type. This may be achieved in any one of a number of ways, such as by having the first processing system 10 retrieve threshold values from the memory 21 and transfer these to the second processing system 17, although any suitable mechanism may be used. In general, multiple thresholds may be used to specify different operating characteristics, for signal parameters such as a maximum current that can be applied to the subject S, the minimum voltage required to determine an impedance measurement, a minimum signal to noise ratio, or the like.

At step 1920 the second processing system 17 will activate the signal generator 11 causing a signal to be applied to the subject S. At step 1930 the response signal at the electrodes 15, 16 is measured using the sensor 12 with signals indicative of the signal being returned to the second processing system 17.

At step 1940 the second processing system 17 compares the at least one parameter of the measured signal to a threshold to determine if the measured signal is acceptable at step 1950. This may involve for example determining if the signal to noise levels within the measured voltage signal are above the minimum threshold, or involve determining if the signal strength is above a minimum value.

If the signal is acceptable, impedance measurements can be performed at step 1960. If not, at step 1970 the second processing system 17 determines whether the applied signal has reached a maximum allowable. If this has occurred, the process ends at step 1990. However, if the maximum signal has not yet been reached, the second processing system 17 will operate to increase the magnitude of the current applied to the subject S at step 1980 before returning to step 1920 to determine a new measured signal.

Accordingly, this allows the current or voltage applied to the subject S to be gradually increased until a suitable signal can be measured to allow impedance values to be determined, or until either a maximum current or voltage value for the subject is reached.

It will be appreciated that the thresholds selected, and the initial current applied to the subject S in step 1420 will typically be selected depending on the nature of the subject. Thus, for example, if the subject is a human it is typical to utilise a lower magnitude current than if the subject is an animal such as a mouse or the like.

Lead Calibration

To assist in interpreting the impedance measurements, it is useful to take into account electrical properties of the connecting leads and associated circuitry.

To achieve this, the leads and corresponding connections can be encoded with a value representing calibration information. This can include, for example, using specific values for respective ones of the resistors in the current source, or buffer circuits shown in FIGS. 4 and 5. Thus for example, the value of the resistors $R_{12}$, $R_{13}$, $R_{26}$ can be selected based on the properties of the corresponding leads.

In this instance, when the leads are connected to the measuring device 1, via the corresponding ADCs 37, 38, the processing modules 32, 33 can interrogate the circuitry using appropriate polling signals to thereby determine the value of corresponding resistor. Once this value has been determined, the second processing system 17 can use this to modify the algorithm used for processing the voltage and current signals to thereby ensure correct impedance values are determined.

In addition to this, the resistance value can also act as a lead identifier, to allow the measuring device to identify the leads and ensure that only genuine authorised leads are utilised. Thus, for example, if the determined resistance value does not correspond to a predetermined value this can be used to indicate that non-genuine leads are being used. In this instance, as the lead quality can have an effect on the accuracy of the resultant impedance analysis, it may desirable to either generate an error message or warning indicating that incorrect leads are in use. Alternatively, the second processing system 17 can be adapted to halt processing of the measured current and voltage signals. This allows the system to ensure that only genuine leads are utilised.

This can further be enhanced by the utilisation of a unique identifier associated with each lead connection circuit. In this instance, a unique identifier can be encoded within an IC provided as part of the current source or voltage buffer circuits. In this instance, the measuring device 1 interrogates the unique identifier and compared to unique identifiers stored either in local memory, or in a central database, allowing genuine leads to be identified.

This process can also be used to monitor the number of times a lead has been used. In this instance, each time a lead is used, data reflecting lead usage is recorded. This allows the leads to have a predesignated use quota life span, and once the number of times the lead is used reaches the quota, further measurements using the leads can be prevented. Similarly, a temporal limitation can be applied by providing an expiry date associated with the lead. This can be based on the date the lead is created, or first used depending on the preferred implementation.

It will be appreciated that when recording lead usage, issues may arise if this is recorded locally. In particular, this could allow a lead to be re-used with a different measuring device. To avoid this, the leads can be configured with an ID which is set by the measuring device on first use. This can be used to limit usage of the leads to a single measuring device.

This can be used to ensure that the leads are correctly replaced in accordance with a predetermined lifespan thereby helping to ensure accuracy of measure impedance values.

Device Updates

Figure 22:
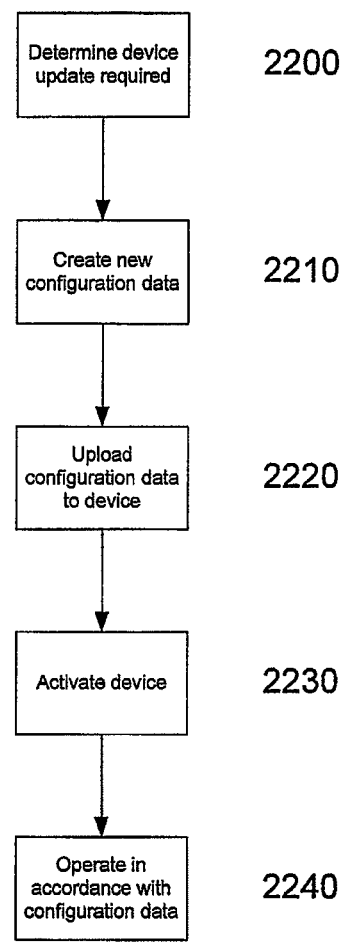
FIG. 22 is a flow chart of an overview of an example of the process of updating a measuring device.

An example of a process for updating the measuring device will now be described with reference to FIG. 22.

In one example, at step 2200 the process involves determining a measuring device 1 is to be configured with an upgrade, or the like, before configuration data is created at step 2210. At step 2220 the configuration data is typically uploaded to the device before the device is activated at 2230. At 2240 when the device commences operation the processing system 2 uses the configuration data to selectively activate features, either for example by controlling the upload of instructions, or by selectively activating instructions embedded within the processing system 2 or the controller 19. This can be achieved in one of two ways. For example, the configuration data could consist of instructions, such as a software or firmware, which when implemented by the processing system 2 causes the feature to be implemented. Thus, for example, this process may be utilised to update the operation of the firmware provided in the second processing system 17, the processing system 10 or the controller 19 to allow additional functionality, improved measuring algorithms, or the like, to be implemented.

Alternatively, the configuration data could be in the form of a list of features, with this being used by the processing system 2 to access instructions already stored on the measuring device 1. Utilisation of configuration data in this manner, allows the measuring device to be loaded with a number of as yet additional features, but non-operational features, when the device is sold. In this example, by updating the configuration data provided on the measuring device 1, this allows these further features to be implemented without requiring return of the measuring device 1 for modification.

This is particularly useful in the medical industry as it allows additional features to be implemented when the feature receives approval for use. Thus, for example, techniques may be available for measuring or detecting lymphoedema in a predetermined way, such as through the use of a particular analysis of measured voltage signals or the like. In this instance when a device is sold, approval may not yet have been obtained from an administering body such as the Therapeutic Goods Administration, or the like. Accordingly, the feature is disabled by appropriate use of a configuration data. When the measurement technique subsequently gains approval, the configuration data can be modified by uploading a new updated configuration data to the measuring device, allowing the feature to be implemented.

It will be appreciated that these techniques may be used to implement any one of a number of different features, such as different measuring techniques, analysis algorithms, reports on results of measured impedance parameters, or the like.

Figure 23:
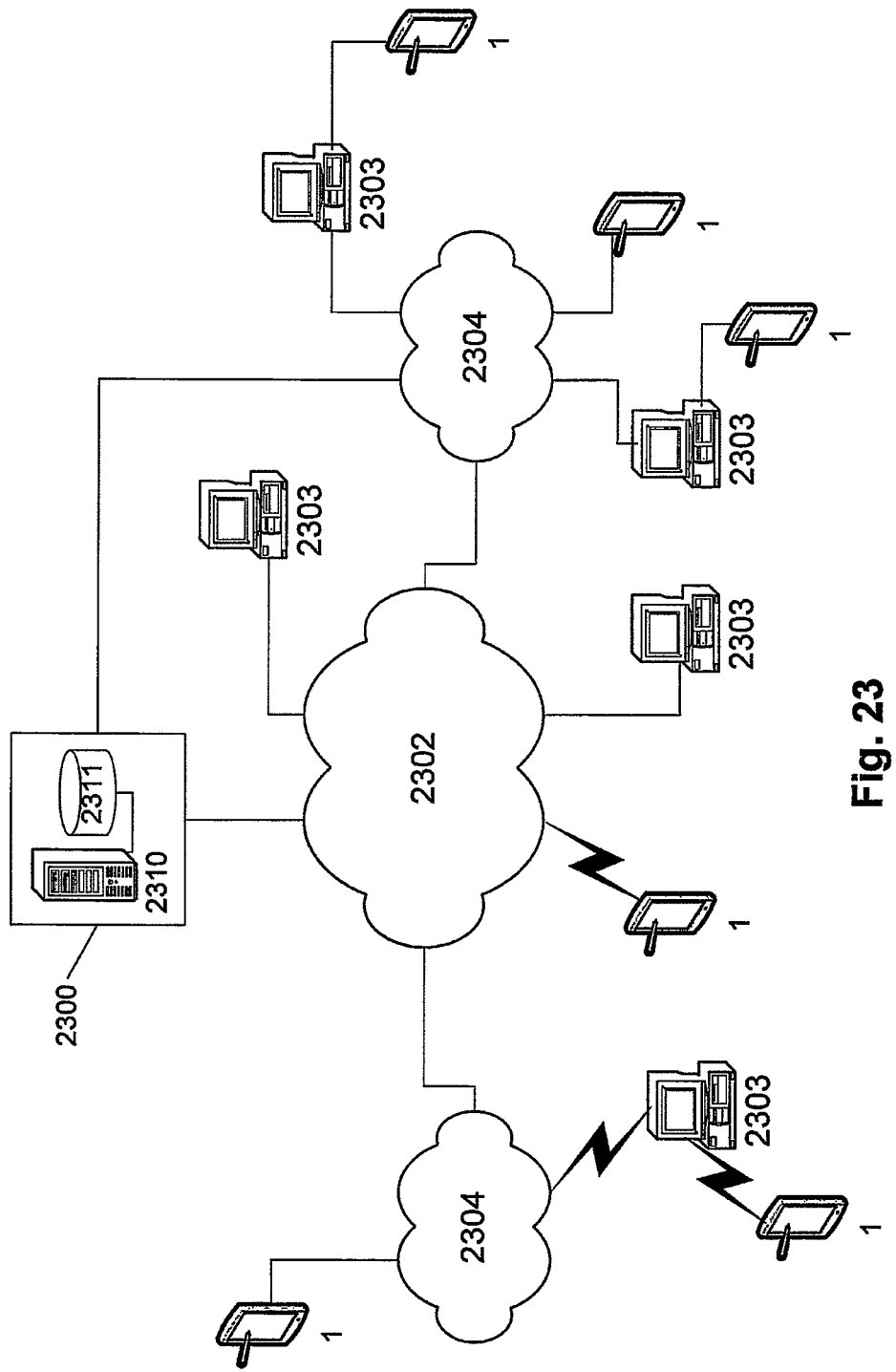
FIG. 23 is a schematic diagram of an example of a system architecture for updating a measuring device.

An example of a suitable system for providing updates will now be described with respect to FIG. 23. In this example, a base station 2300 is coupled to a number of measuring devices 1, and a number of end stations 2303 via a communications network 2302, such as the Internet, and/or via communications networks 2304, such as local area networks (LANs), or wide area networks (WANs). The end stations are in turn coupled to measuring devices 1, as shown.

In use, the base station 2300 includes a processing system 2310, coupled to a database 2311. The base station 2300 operates to determine when updates are required, select the devices to which updates are applied, generate the configuration data and provide this for update to the devices 1. It will be appreciated that the processing system 2310 may therefore be a server or the like.

This allows the configuration data to be uploaded from the server either to a users end station 2303, such as a desk top computer, lap top, Internet terminal or the like, or alternatively allows transfer from the server via the communications network 2302, 2304, such as the Internet. It will be appreciated that any suitable communications system can be used such as wireless links, wi-fi connections, or the like.

Figure 24:
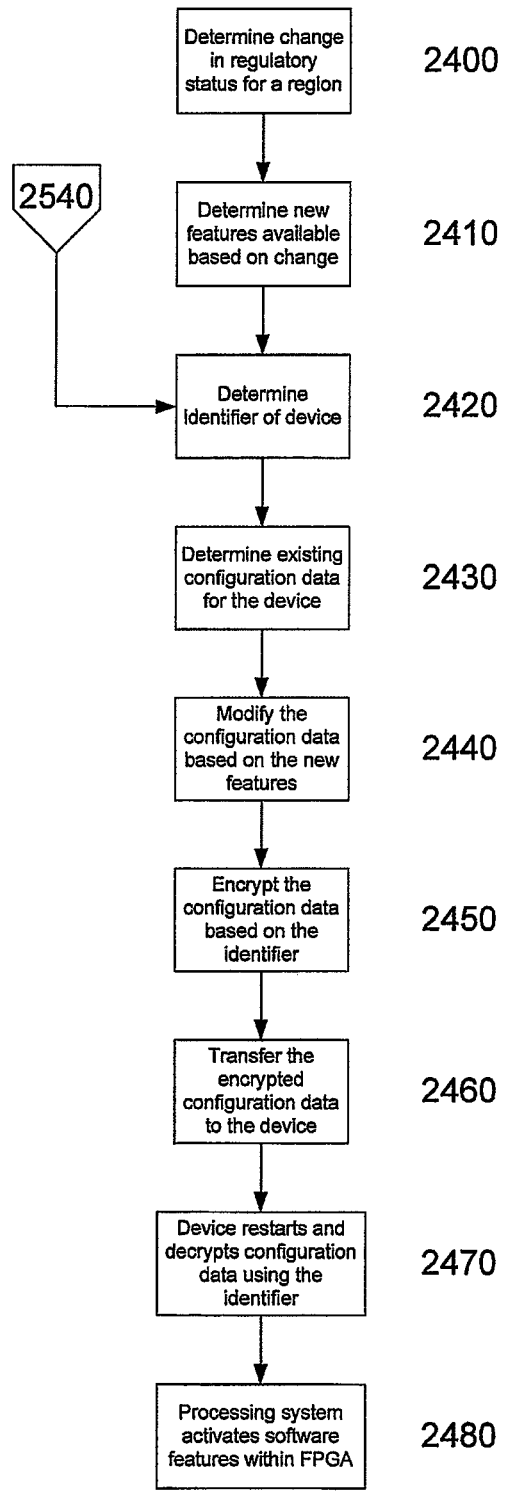
FIG. 24 is a flow chart of a first example of the process of updating a measuring device; and,
FIG. 25 is a flow chart of a second example of the process of updating a measuring device.

In any event, an example of the process of updating the measuring device 1 will now be described in more detail with reference to FIG. 24. In this example, at step 2400 the base station 2300 determines that there is a change in the regulatory status of features implemented within a certain region. As mentioned above this could occur for example following approval by the TGA of new features.

The base station 2300 uses the change in regulatory status to determine new features available at step 2410, before determining an identifier associated with each measuring device 1 to be updated at step 2420. As changes in regulatory approval are region specific, this is typically achieved by having the base station 2300 access database 2311 including details of the regions in which each measuring device sold are used. The database 2311 includes the identifier for each measuring device 1, thereby allowing the identifier of each measuring device to be updated to be determined.

At step 2430, the base station 2300 determines the existing configuration data, typically from the database 2311, for a next one of the measuring devices 1, before modifying the configuration data to implement the new features at step 2440. The configuration data is then encrypted utilizing a key associated with the identifier at step 2450. The key may be formed from a unique prime number associated with the serial number, or partially derived from the serial number, and is typically stored in the database 2311, or generated each time it is required using a predetermined algorithm.

At step 2460 the encrypted configuration data is transferred to the measuring device 1 as described above.

At step 2470 when the device rests and the first processing system 10 is activated, the first processing system 10 determines the encryption key, and uses this to decrypt the configuration data. This may be achieved in any one of a number of ways, such as by generating the key using the serial number or other identifier, and a predetermined algorithm. Alternatively, this may be achieved by accessing a key stored in the memory 21. It will be appreciated that any form of encryption may be used, although typically strong encryption is used, in which a secret key is used to both encrypt and decrypt the configuration data, to thereby prevent fraudulent alteration of the configuration by users, as will be explained in more detail below.

At step 2480, the first processing system 10 activates software features within the second processing system 24 using the decrypted configuration data.

It will therefore be appreciated that this provides a mechanism for automatically updating the features available on the measuring device. This may be achieved either by having the second processing system 24 receive new firmware from the processing system 10, or by activating firmware already installed on the second processing system 24, as described above.

As an alternative to performing this automatically when additional features are approved for use, the process can be used to allow features to be activated on payment of a fee. In this example, a user may purchase a measuring device 1 with limited implemented functionality. By payment of a fee, additional features can then be activated as and when required by the user.

Figure 25:
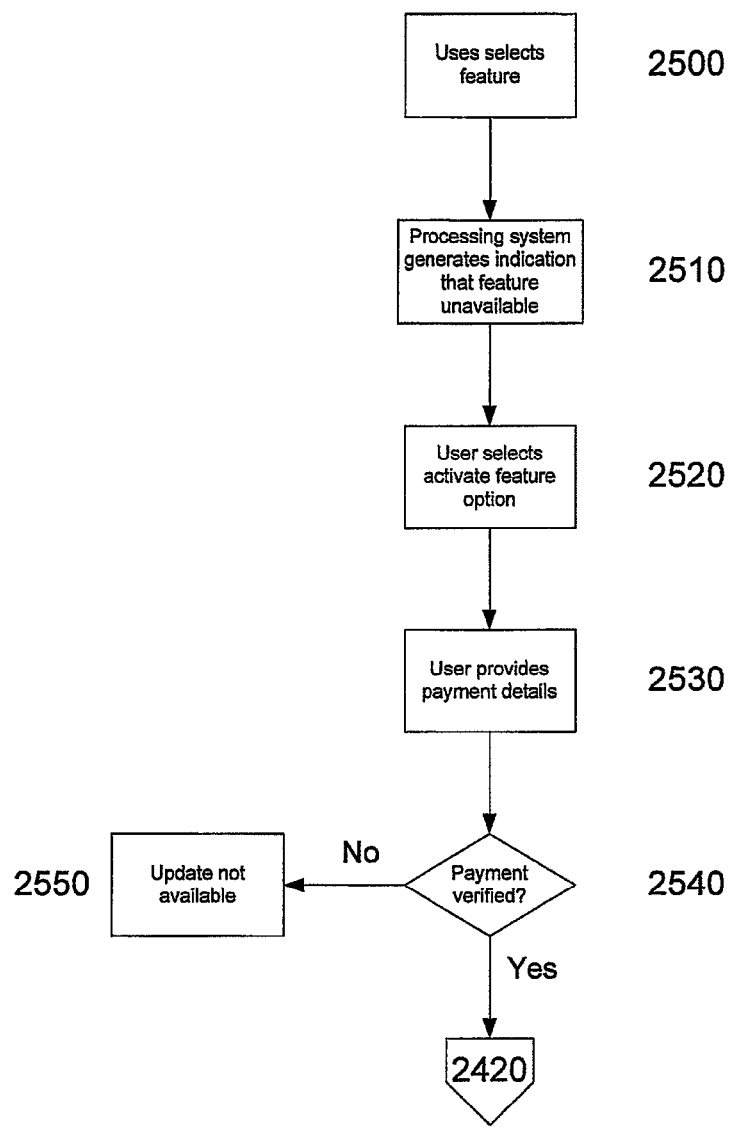

In this example, as shown in FIG. 25, when the user selects an inactive feature at step 2500, the first processing system 10 will generate an indication that the feature is unavailable at step 2510. This allows the user to select an activate feature option at step 2520, which typically prompts the user to provide payment details at step 2530. The payment details are provided to the device manufacturer in some manner and may involve having the user phone the device manufacturer, or alternatively enter the details via a suitable payment system provided via the Internet or the like.

At step 2540, once the payment is verified, the process can move to step 2420 to allow an automatic update to be provided in the form of a suitable configuration data. However, if payment details are not verified the process ends at 2550.

It will be appreciated by a person skilled in the art that encrypting the configuration data utilising a unique identifier means that the configuration data received by a measuring device 1 is specific to that measuring device. Accordingly, the first processing system 10 can only interpret the content of a configuration data if it is both encrypted and decrypted utilising the correct key. Accordingly, this prevents users exchanging configuration data, or attempting to re-encrypt a decrypted file for transfer to a different device.

It will be appreciated that in addition to, or as an alternative to simply specifying features in the configuration data, it may be necessary to upload additional firmware to the second processing system 24. This can be used for example, to implement features that could not be implemented using the firmware shipped with the measuring device 1.

In this example, it would be typical for the configuration data to include any required firmware to be uploaded, allowing this to be loaded into the second processing system 24, using the first processing system 10. This firmware can then either be automatically implemented, or implemented in accordance with the list of available features provided in the configuration data.

It will be appreciated that this provides a mechanism for updating and/or selectively activating or deactivating features, such as measuring protocols, impedance analysis algorithms, reports interpreting measured results, or the like. This can be performed to ensure the measuring device conforms to existing TGA or FDA approvals, or the like.

The end station 2303 can effectively perform any one or more of tasks performed by the first processing system 10 in the examples throughout the specification. Accordingly, the device could be provided without the first processing system 10, with the functionality usually performed by the first processing system 10 being performed by an end station 2303. In this arrangement, the end station 2303 therefore effectively forms part or all of the first processing system 10. This allows the measuring device 1 to be provided including only the second processing system 17 coupled directly to the external interface 23 to allow the measuring device 1 to be controlled by the end station 2303. This would typically be achieved via the use of suitable applications software installed on the end station 2303.

Persons skilled in the art will appreciate that numerous variations and modifications will become apparent. All such variations and modifications which become apparent to persons skilled in the art, should be considered to fall within the spirit and scope that the invention broadly appearing before described.

Thus, for example, it will be appreciated that features from different examples above may be used interchangeably where appropriate. Furthermore, whilst the above examples have focussed on a subject such as a human, it will be appreciated that the measuring device and techniques described above can be used with any animal, including but not limited to, primates, livestock, performance animals, such race horses, or the like.

The above described processes can be used for diagnosing the presence, absence or degree of a range of conditions and illnesses, including, but not limited to oedema, pulmonary oedema, lymphoedema, body composition, cardiac function, and the like.

It will also be appreciated above described techniques, such as electrode identification, device updates and the like may be implemented using devices that do not utilise the separate first processing system 10 and second processing system 17, but rather use a single processing system 2, or use some other internal configuration.

The invention claimed is:

1. Apparatus for connecting an impedance measurement apparatus to an electrode, the apparatus including:
   a) a housing having a connector for coupling the housing to the electrode; and
   b) a circuit mounted in the housing, the circuit being electrically coupled to the electrode using the connector, and being coupled to the impedance measurement apparatus via a lead, the circuit including a current source circuit configured to:
      a) receive one or more control signals from the impedance measurement apparatus via the lead;
      b) filter and amplify the control signals to thereby generate one or more current signals;
      c) apply the current signals to the electrode; and
      d) transfer an indication of the applied signals to the impedance measurement apparatus.

2. Apparatus according to claim 1, wherein the circuit is provided on a circuit board having an electrical contact, and wherein in use the connector urges at least part of the electrode into abutment with the electrical contact.

3. Apparatus according to claim 2, wherein the connector includes a biased arm.

4. Apparatus according to claim 1, wherein the circuit includes a buffer circuit configured to:
   a) sense voltage signals at the electrode;
   b) filter and amplify the voltage signals; and
   c) transfer the filtered and amplified voltage signals to the impedance measurement apparatus.

5. Apparatus according to claim 1, wherein the apparatus further comprises the electrode, the electrode including:
   a) an electrode substrate; and
   b) a conductive material for electrically coupling the electrode to a subject.

6. Apparatus according to claim 5, wherein the electrode substrate is electrically conductive, and wherein in use the connector couples the circuit to the electrode substrate.

7. Apparatus according to claim 1, wherein the housing includes curved edges.

8. Apparatus according to claim 1, wherein the housing is formed from a material that:
   a) has a low coefficient of friction; or
   b) is resilient.

9. Apparatus for connecting an impedance measurement apparatus to an electrode, the apparatus including:
   a) a housing having a connector for coupling the housing to the electrode;
   b) a circuit mounted in the housing, the circuit being provided on a circuit board having an electrical contact for electrically coupling the circuit and the electrode, the circuit being coupled to the impedance measurement apparatus via a lead, the circuit including a current source circuit configured to:
      a) receive one or more control signals from the impedance measurement apparatus via a lead;
      b) filter and amplify the control signals to thereby generate one or more current signals;
      c) apply the current signals to the electrode; and
      d) transfer an indication of the applied signals to the impedance measurement apparatus; and
   c) a biased arm, the biased arm being for urging at least part of the electrode into abutment with the electrical contact.

10. Apparatus for connecting an impedance measurement apparatus to an electrode including a conductive electrode substrate, the apparatus including:
   a) a housing having a connector for coupling the housing to the electrode;
   b) a circuit mounted in the housing, the circuit being provided on a circuit board having an electrical contact for electrically coupling the circuit and the electrode, the circuit being coupled to the impedance measurement apparatus via a lead, the circuit including a current source circuit configured to:
      a) receive one or more control signals from the impedance measurement apparatus via a lead;
      b) filter and amplify the control signals to thereby generate one or more current signals;
      c) apply the current signals to the electrode; and
      d) transfer an indication of the applied signals to the impedance measurement apparatus; and
   c) a biased arm, the biased arm being for urging the conductive electrode substrate into abutment with the electrical contact.

* * * * *